US012458763B2

(12) United States Patent
Baumann et al.

(10) Patent No.: US 12,458,763 B2
(45) Date of Patent: Nov. 4, 2025

(54) APPARATUS FOR PRODUCING AEROSOLS

(71) Applicant: Loewenstein Medical Technology S.A., Luxembourg (LU)

(72) Inventors: Josef Baumann, Passau (DE); Peter Kremeier, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 832 days.

(21) Appl. No.: 17/804,331

(22) Filed: May 27, 2022

(65) Prior Publication Data

US 2022/0379045 A1 Dec. 1, 2022

(30) Foreign Application Priority Data

May 28, 2021 (DE) ......................... 102021002767.1

(51) Int. Cl.

| | |
|---|---|
| ***A61M 11/00*** | (2006.01) |
| ***A61M 16/08*** | (2006.01) |
| ***B05B 17/06*** | (2006.01) |

(52) U.S. Cl.

CPC ...... *A61M 11/005* (2013.01); *A61M 16/0833* (2014.02); *B05B 17/0669* (2013.01)

(58) Field of Classification Search

CPC . A61M 11/005; A61M 15/0085; B05B 17/06; B05B 17/0607; B05B 17/0646; B05B 17/0669

See application file for complete search history.

(56) References Cited

U.S. PATENT DOCUMENTS

| | | | |
|---|---|---|---|
| 2005/0011514 A1* | 1/2005 | Power .................. | A61M 11/005 128/200.14 |
| 2013/0291859 A1 | 11/2013 | Casey et al. | |
| 2016/0228903 A1 | 8/2016 | Redjdal et al. | |
| 2017/0072160 A1 | 3/2017 | Gordon et al. | |
| 2021/0020823 A1* | 1/2021 | Kang ................ | A61M 15/0021 |
| 2021/0106064 A1* | 4/2021 | Akao ...................... | A24F 40/53 |
| 2021/0212381 A1* | 7/2021 | Lau ........................ | G11C 17/18 |

* cited by examiner

*Primary Examiner* — Kendra D Carter
*Assistant Examiner* — Jaeick Jang
(74) *Attorney, Agent, or Firm* — Abel Schillinger, LLP

(57) ABSTRACT

A nebulizer for producing an inhalable mist of droplets, comprising at least an aerosol generator, a housing having a liquid reservoir and control electronics, the aerosol generator consisting at least of a membrane, a piezo element and a substrate plate, and the control electronics comprising at least an RF generator, a controller, memory and switching elements, and an inductor. The aerosol generator forms a resonant circuit together with the inductor and the control electronics are configured to at least partly excite the aerosol generator to vibrate. The aerosol generator is configured such that aerosol droplets are producible by vibrations and the RF generator is configured to vary the amount of aerosol produced.

19 Claims, 11 Drawing Sheets

APPARATUS FOR PRODUCING AEROSOLS

CROSS-REFERENCE TO RELATED APPLICATIONS

The present application claims priority under 35 U.S.C. § 119 of German Patent Application No. 102021002767.1, filed May 28, 2021, the entire disclosure of which is expressly incorporated by reference herein.

BACKGROUND OF THE INVENTION

1. Field of the Invention

The invention relates to an apparatus for producing aerosols, and to a method and component for adjusting the amount of aerosol.

2. Discussion of Background Information

Compared to other nebulizer technology, such as jet nebulizers or ultrasonic nebulizers, vibrating mesh nebulizers have substantial advantages. Thus, a very fine primary aerosol can be produced as a result of the aerosol production by means of micro-holes. This largely prevents the larger droplets being deposited before the aerosol is inhaled. As a result, a greater proportion of the poured-in medicament can reach the deep regions of the lung.

The commercially available systems are constrained in that the ejection of the aerosol cannot be adjusted. When applying different medicaments, it may be advantageous to adjust the administration rate to the metering requirements of the medicament. By way of example, it may be advantageous for a medicament not to flood into the body too quickly. However, an adjustment of the aerosol administration rate is currently connected to a technical change (e.g., reducing the holes in the membrane). This means a significant developmental and regulatory outlay and is connected to a technical multiplication of the components.

In view of the foregoing, it would be advantageous to have available a system which is easy to handle and covers a broad spectrum of use.

SUMMARY OF THE INVENTION

The nebulizer according to the invention for producing an inhalable mist of droplets (aerosol) comprises at least an aerosol generator, a housing having a liquid reservoir and control electronics. The aerosol generator consists at least of a membrane, a piezo element and a substrate plate. The control electronics comprise at least an RF generator, a controller, memory and switching elements, and an inductor. The aerosol generator forms a resonant circuit together with the inductor and the control electronics are configured so that they at least partly excite the aerosol generator to vibrate. The aerosol generator is configured such that aerosol droplets are producible by the vibrations and the RF generator is configured to vary the amount of aerosol produced.

In some embodiments, the nebulizer is also characterized in that the RF generator produces rectangular signals with a pulse width as RF signal.

In some embodiments, the nebulizer is also characterized in that the memory and switching elements of the control electronics are configured to produce an excitation signal from the rectangular signal and the resonant circuit.

In some embodiments, the nebulizer is also characterized in that the memory and switching elements comprise at least a transformer and a transistor.

In some embodiments, the nebulizer is also characterized in that the transistor is configured, in conjunction with the transformer, to produce an excitation signal from the rectangular signal and the resonant circuit.

In some embodiments, the nebulizer is also characterized in that the control electronics are configured to specify an excitation frequency for the aerosol generator and/or the resonant circuit.

In some embodiments, the nebulizer is also characterized in that the control electronics are configured to produce a sinusoidal excitation signal.

In some embodiments, the nebulizer is also characterized in that the produced excitation signal has a higher voltage than the rectangular signal.

In some embodiments, the nebulizer is also characterized in that the nebulizer is configured to control the amount of aerosol produced by way of the pulse width.

In some embodiments, the nebulizer is also characterized in that the pulse width of the rectangular signal reaches a maximum of about 50%.

In some embodiments, the nebulizer is also characterized in that the pulse width of the rectangular signal reaches a maximum of about 30%.

In some embodiments, the nebulizer is also characterized in that the RF generator comprises at least an oscillator and a pulse width modulator, the pulse width modulator being configured to specify the pulse width of the rectangular signal.

In some embodiments, the nebulizer is also characterized in that the control electronics comprise at least a device for measuring a voltage, the device for measuring the voltage being arranged such that the voltage is recorded at the aerosol generator and the control electronics being configured to determine the optimal frequency of the excitation signal from the voltage measurement.

In some embodiments, the nebulizer is also characterized in that the control electronics are configured to determine the optimal excitation frequency by way of a voltage drop at the aerosol generator when the optimal excitation frequency is overshot.

In some embodiments, the nebulizer is also characterized in that the optimal excitation frequency corresponds to the resonant frequency of the aerosol generator and/or of the resonant circuit.

In some embodiments, the nebulizer is also characterized in that the control electronics are configured to automatically determine the optimal excitation frequency and/or resonant frequency of the aerosol generator and/or resonant circuit.

In some embodiments, the nebulizer is also characterized in that the control electronics are configured to regularly check and automatically adjust the optimal excitation frequency.

In some embodiments, the nebulizer is also characterized in that the control electronics comprise at least a device for measuring the current intensity on the primary and/or secondary side of the transformer and the control electronics are configured to determine a power on the primary and/or secondary side of the transformer by way of the voltage and the measured current intensity.

In some embodiments, the nebulizer is also characterized in that the control electronics are configured to determine the efficiency by way of a comparison of the determined power on the primary side of the transformer with the determined power on the secondary side of the transformer.

In some embodiments, the nebulizer is also characterized in that the control electronics are configured to determine a maximum efficiency on the basis of the comparison of the powers of the transformer on the primary and secondary sides.

In some embodiments, the nebulizer is also characterized in that the control electronics are configured to link the maximum efficiency to the pulse width.

In some embodiments, the nebulizer is also characterized in that the nebulizer is connectable to a ventilator and the control electronics are configured to receive and implement specifications regarding the aerosol production from the ventilator.

In some embodiments, the nebulizer is also characterized in that the nebulizer comprises a nebulizer part and an electronics part.

In some embodiments, the nebulizer is also characterized in that the nebulizer part comprises at least the aerosol generator and the liquid reservoir, the liquid reservoir being formed in such a way that a liquid is led to the membrane of the aerosol generator.

In some embodiments, the nebulizer is also characterized in that the electronics part comprises at least the control electronics.

In some embodiments, the nebulizer is also characterized in that the aerosol generator is mounted in a frame in the nebulizer part, the frame comprising at least one opening through which the liquid is led to the membrane, and in that the liquid reservoir is separated from an insertion opening for the electronics part by way of a wall, the wall terminating with the edge of the opening.

The present invention also provides a method for adjusting the aerosol production of a nebulizer and in particular, the nebulizer set forth above, comprising at least one of the following steps:

finding the resonant frequency of the aerosol generator and/or of the resonant circuit,
determining the optimal efficiency,
adjusting the pulse width,
adjusting the amount of aerosol produced/to be produced.

In some embodiments, the method is also characterized in that, for the purposes of finding the resonant frequency of the aerosol generator and/or of the resonant circuit, a range of excitation frequencies is sampled and, at the same time, the voltage at the aerosol generator is measured, the resonant frequency being reached when an increase in the excitation frequency leads to a drop in the measured voltage.

In some embodiments, the method is also characterized in that the determination of the optimal efficiency comprises a measurement of the current intensity at the primary side and at the secondary side of the transformer, and a respective power for the primary side and for the secondary side is determined from the respective current intensity by way of the voltage, and an efficiency is determined from a comparison of the determined powers.

In some embodiments, the method is also characterized in that the determination of the optimal efficiency further comprises a variation in the pulse width, a variation in the efficiency following a variation of the pulse width and the greatest determined efficiency being considered to be the optimal efficiency.

In some embodiments, the method is also characterized in that the optimal efficiency is related to the specified pulse width.

In some embodiments, the method is also characterized in that the adjustment of the amount of aerosol produced/to be produced comprises a variation of the pulse width, a reduction in the pulse width below the pulse width for the optimal efficiency resulting in a reduction of the amount of aerosol produced.

The present invention further provides a ventilation system comprising at least a ventilator and a nebulizer as set forth above, wherein the ventilation system at least comprises control electronics for controlling the nebulizer.

The ventilation system is also characterized in that the control electronics are at least partly arranged in that nebulizer.

Also provided is a ventilator for use in the ventilation system, characterized in that the ventilator comprises at least a control unit that is configured to transmit specifications relating to the aerosol production to the control electronics, the specifications comprising at least a setting regarding the amount, duration and/or time of the aerosol production.

Attention should be drawn to the fact that the features listed individually in the claims can be combined with one another in any technically expedient fashion and indicate further configurations of the invention. The description provides additional characterization and specification of the invention, particularly in conjunction with the figures.

Is also should be appreciated that an "and/or" conjunction used herein, found between two features and linking these should always be interpreted such that only the first feature may be present in a first configuration of the subject matter of the invention, only the second feature may be present in a second configuration, and both the first and the second feature may be present in a third configuration.

A ventilator is to be understood to mean any device which assists a user or patient with natural respiration, undertakes the ventilation of the user or living being (e.g., patient and/or newborn and/or premature baby) and/or is used for respiratory therapy and/or influences the respiration of the user or patient in another way. By way of example, but without being an exhaustive list, these include CPAP and BiPAP machines, anesthetic machines, respiratory therapy devices, (clinical, outpatient or emergency) ventilators, high-flow therapy devices and cough machines. Ventilators can also be understood to mean diagnostic devices for ventilation. Said diagnostic devices can generally be used to measure medical and/or respiration-based parameters of a living being. These also include devices which can measure and optionally process medical parameters of patients in combination with respiration or only in relation to respiration.

Unless expressly described otherwise, a patient interface can be understood to mean any peripheral device which is designed for interaction of the measurement device with a living being, in particular for therapeutic or diagnostic purposes. In particular, a patient interface can be understood to mean a mask of a ventilator or a mask connected to the ventilator. Said mask can be a full-face mask, i.e., a mask surrounding the nose and mouth, or a nasal mask, i.e., a mask only surrounding the nose. Tracheal tubes or cannulas and so-called nasal cannulas can be used as a mask or patient interface, too. To this end, high-flow masks or high-flow interfaces may also be subsumed by the term patient interface. In some cases, the patient interface can also be a simple mouthpiece, for example a tube, through which the living being at least exhales and/or inhales.

It should further be noted that the term amount of aerosol produced relates to the amount of aerosol produced per membrane movement period, unless expressly stated otherwise. The term pulse width is used synonymously for the term width of the pulse; both terms denote the same. The term pulse duration can also be considered to be synonymous.

In particular, the invention relates to a nebulizer, to control electronics for a nebulizer, and to a method for controlling a nebulizer. What is particularly advantageous here is that the amount of aerosol produced by the nebulizer is easily and efficiently adjustable without needing to interchange any components of said nebulizer.

The resonant system, for example the resonant circuit consisting of the aerosol generator and the inductor, is excited by a periodic signal which is produced in an electronic circuit, for example in the control electronics. According to the invention, an advantageous set up the control electronics is presented, by means of which the aerosol generation can be easily influenced and optimized. By way of example, what can be achieved is that the excitation frequency can be defined in such a way that a high aerosol generation rate or generation amount can be obtained for low power requirements. In this context, the efficiency can also be optimized by simple closed-loop control.

In particular, the aerosol production can be adjustable over a broad range purely by way of software inputs. By way of example, the software is configured so that the specifications are transmitted to the control electronics via a control unit. In particular, very different forms of application, product variants and/or fields of use are realizable by way of these specifications via software and/or a control unit, for example in appropriately configured ventilators, without this requiring changes to the hardware, such as the installed membrane.

In some embodiments, the nebulizer has an at least two-part embodiment and comprises a nebulizer part and an electronics part. By way of example, the nebulizer part can be in the form of a disposable product and used only for one patient over a certain period of time, and can subsequently be disposed of. By way of example, only components which are absolutely necessary, such as the aerosol generator and the liquid reservoir, are therefore installed therein. The individual parts of the nebulizer part can be assembled, for example, by way of simple joining steps (positioning, then pressing together and/or latching).

By contrast, the electronics part as a rule is reusable and can be used for multiple patients. In some embodiments, the electronics part comprises at least parts of the control electronics. Since the electronics are integrated in the connecting part, additional components, such as plugs, cables, etc., are dispensed with. Moreover, the risk of electromagnetic incompatibility (EMC) is minimized since only low-power signals and the power supply are guided over the cable.

An O-ring, for example, seals the connection between electronics part and nebulizer part. In some embodiments, the O-ring simultaneously also seals the electronics part.

By way of example, the electronics part and the nebulizer part are easily and intuitively connectable by way of a latching mechanism.

The frame holds the aerosol generator in position with minimal clamping forces, seals the medicament reservoir with respect to the flange/the connecting piece and seals the medicament reservoir with respect to the aerosol generator.

The invention also relates to a method for controlling the aerosol production. In this case, the method comprises at least one of the steps of finding the resonant frequency of the aerosol generator, determining the optimal efficiency and/or adjusting the pulse width and/or adjusting the amount of aerosol produced/to be produced.

The resonant frequency of the aerosol generator is determined by the specification of the various excitation frequencies and the simultaneous determination of the voltage at the aerosol generator or the resonant circuit. The resonant frequency has been reached at a maximum measured voltage. The resonant frequency is also characterized in that the measured voltage reduces when the resonant frequency is overshot and/or undershot.

The optimal efficiency of the aerosol generator is determined by current measurements on the primary side and the secondary side of the transformer. The optimal efficiency can be set by adjusting the pulse width. The efficiency arises from the ratio of measured/determined power on the primary side to the power on the secondary side of the transformer. By way of example, the power can be determined by way of the voltage and the respective current intensity on the primary side and/or secondary side of the transformer.

The amount of aerosol to be produced is attained by adjusting the pulse width of the RF signal. Within certain limits, a greater pulse width leads to a greater amount of aerosol produced. A smaller pulse width yields a smaller amount of aerosol produced. The pulse width of the pulses applied to the transformer in this case control the energy input into the resonant system of the aerosol generator. In this case, a greater pulse width thus corresponds to higher energy input.

BRIEF DESCRIPTION OF THE DRAWINGS

The invention will be described in more detail and by way of example on the basis of the accompanying drawings, in which.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
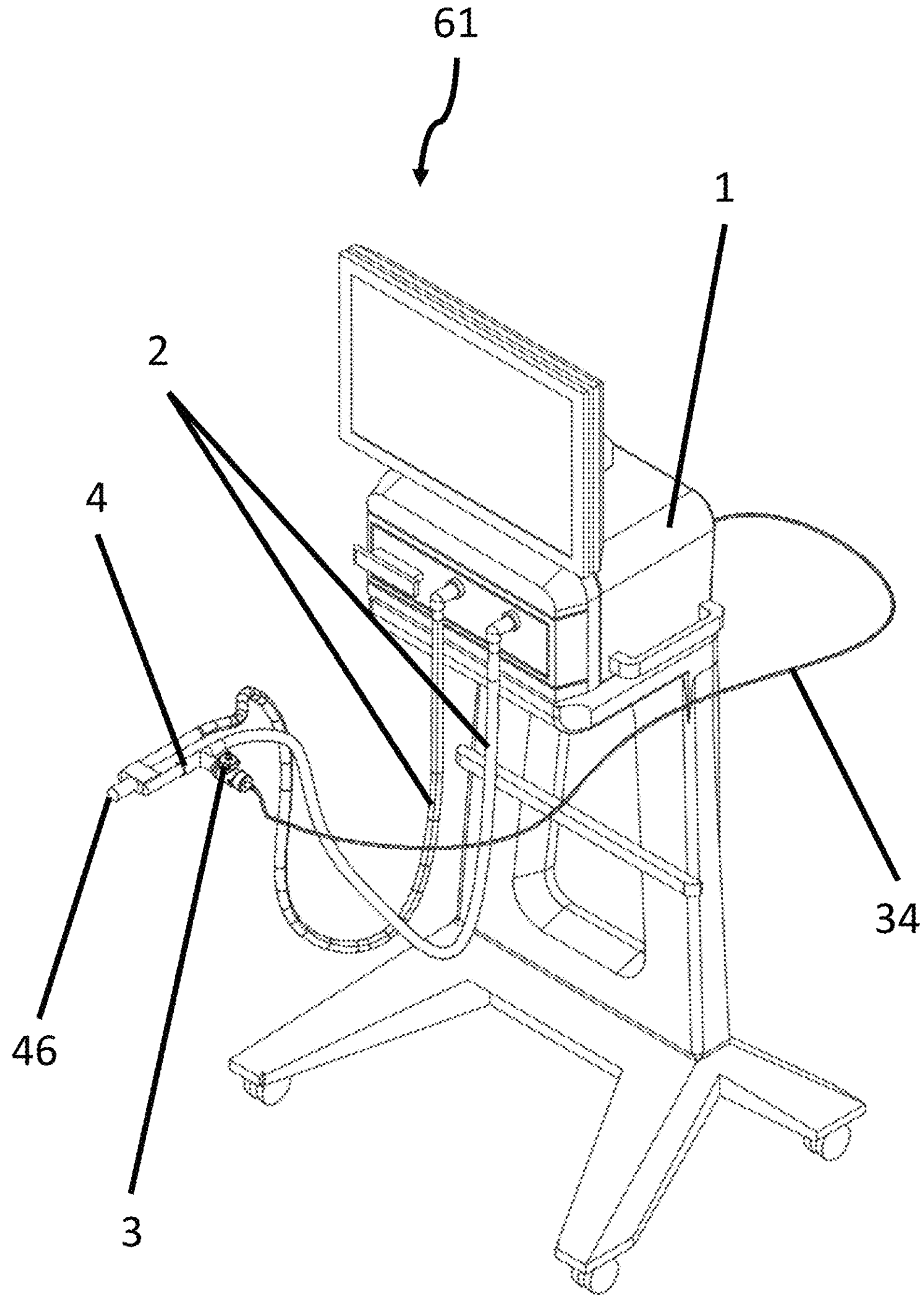
FIG. 1 shows a ventilator which is connected to a nebulizer in a ventilation system.

FIG. 1 depicts a ventilator 1, which is connected to the nebulizer 3 in a ventilation system 61. By way of example, the ventilator 1 is configured to deliver a respiratory gas flow to a patient via a tube 2. In this case, the connection to the patient is implemented by way of a patient interface, for example, the latter for example being connected to the tube system and the ventilator 1 by way of a mask connector 46. The ventilator 1 shown in exemplary fashion comprises a two-tube system, respiratory gas being delivered to the patient through one tube 2 and the exhaled respiratory gas being conducted away from the patient through the other tube. In addition to such a two-tube system, other types of connection between patient and ventilator 1 can also be used, for example connections comprising a leakage system through which the patient exhales.

The ventilator 1 comprises at least one user interface, by means of which it is possible to at least input data, information and/or specifications, which relate to the ventilation and optionally the production of aerosol by the nebulizer 3.

By way of example, the ventilator 1 is configured to assist the patient with respiration and/or to prescribe the respiration for the patient and/or to carry out artificial ventilation. To this end, the ventilator 1 comprises at least one respiratory gas source for providing respiratory gas, with additional gas sources, for example for oxygen, optionally also being able to be used or being integrated in the ventilator 1. In this case, the respiratory gas can be delivered to the patient under pressure and/or flow control, with the ventilator 1 comprising appropriate control and sensor units. Moreover, the ventilator 1 is designed and configured to recognize respiratory phases, for example inspiration and expiration, and control the provision of the respiratory gas on the basis of the respiratory phase. The ventilator 1 may also be designed to recognize various respiratory tract problems, for example blockages of the respiratory tract, apnea, etc., and to subsequently adjust the respiratory gas control. By way of example, the ventilator 1 also comprises a control unit, by means of which specifications relating to the aerosol generation are transmitted to the control electronics 13.

The nebulizer 3 according to the invention is preferably connected to the tube 2 through which the respiratory gas is delivered to the patient during inspiration. Advantageously, the nebulizer 3 is arranged as close as possible to the mask connector 46. By way of example, the nebulizer 3 is connected to the tube 2 for inspiration by way of a tee joint 4. For power supply and transmission of signals, for example for nebulizer 3 control, the nebulizer 3 is connected to the ventilator 1 by way of a cable 34. In some embodiments, the nebulizer 3 is supplied with power by way of an external and/or integrated rechargeable battery/battery.

The nebulizer 3 is designed as a vibrating mesh nebulizer. To this end, the nebulizer 3 comprises at least an aerosol generator 16—at least consisting of a substrate plate 7, a perforated membrane 5 and a piezo element 6—by means of which an aerosol can be produced by nebulization of a liquid 9. To this end, the membrane 5 above the piezo element 6 is made to vibrate, with a liquid 9 being led to the membrane 5 from one side of the membrane 5, the liquid being pressed through the apertures 14 of the membrane 5 or the membrane 5 being pressed against the liquid 9, as a result of which the liquid 9 is partly pressed through the apertures 14 and detaches into small aerosol droplets 15. In this case, the liquid 9 can be any liquid medium, including dissolved substances. In particular, medicaments and/or active ingredients, and the solutions, mixtures and/or dilutions thereof are usable as liquid 9. Suspensions and/or emulsions are also usable as liquid 9 in some embodiments, wherein, in the case of suspensions in particular, the particle dimension should not exceed the dimension of the apertures 14.

By way of example, stainless steel can be used as a material for the membrane 5. By way of example, a stainless-steel membrane is structured in a laser process. Nickel and/or nickel-palladium alloys and/or other metals/metal alloys are also conceivable as membrane materials in some embodiments. By way of example, membranes made of nickel and/or nickel-palladium alloys can be produced by way of an electroforming method. In principle, other materials, for example plastics/polymers and/or silicon, may also be used as membrane materials.

The ventilator 1 can transmit control signals to the nebulizer 3 by way of the cable 34. By way of example, this can control when the nebulizer 3 should produce an aerosol. The duration of aerosol production and the amount of aerosol produced can also for example be specified by the ventilator 1. By way of example, the control electronics 13 of the nebulizer 3 are configured so as to appropriately interpret and implement the signals from the ventilator 1. In some embodiments, the ventilator 1 can also transmit sensor data, for example pressure and/or flow data, to the nebulizer 3, the control electronics 13 of the nebulizer 3 being configured to interpret the sensor data and independently determine time, duration, and/or amount of aerosol production. In some embodiments, the control electronics 13 may also be arranged at least in part in the ventilator 1. By way of example, only electrical pulses are then transmitted to the nebulizer 3.

By way of example, the ventilator 1 is configured so that the nebulizer 3 is driven for aerosol production on the basis of the respiratory cycle. In some cases, aerosol is only produced for the inspiration, for example. To this end, the aerosol production also be started with the start of inspiration, for example. It is also conceivable for example to start with the aerosol production just before the end of the expiration so that a certain amount of aerosol is already available at the start of the inspiration. By way of example, the aerosol production may also already be terminated before the end of the inspiration, for example if the respiratory flow reduces toward the end of the inspiration and aerosol would hardly still be breathed in. A control on the basis of recognized respiratory problems may also be possible.

Provision can also be made for the ventilator 1 and/or the nebulizer 3 to control the amount of aerosol to be produced on the basis of further medical data and/or specifications. In some embodiments, a time-controlled aerosol production, for example, can be set up; by way of example, a certain amount of aerosol is produced at certain times, for example as a regular medicament administration. In some embodiments, the ventilator 1 and/or the nebulizer 3 is for example supplied with further medical and/or physiological data—e.g., heart rate, oxygen saturation, sleep/awake phases, body temperature, etc.—whereupon the aerosol production is adjusted and/or activated.

Figure 2:
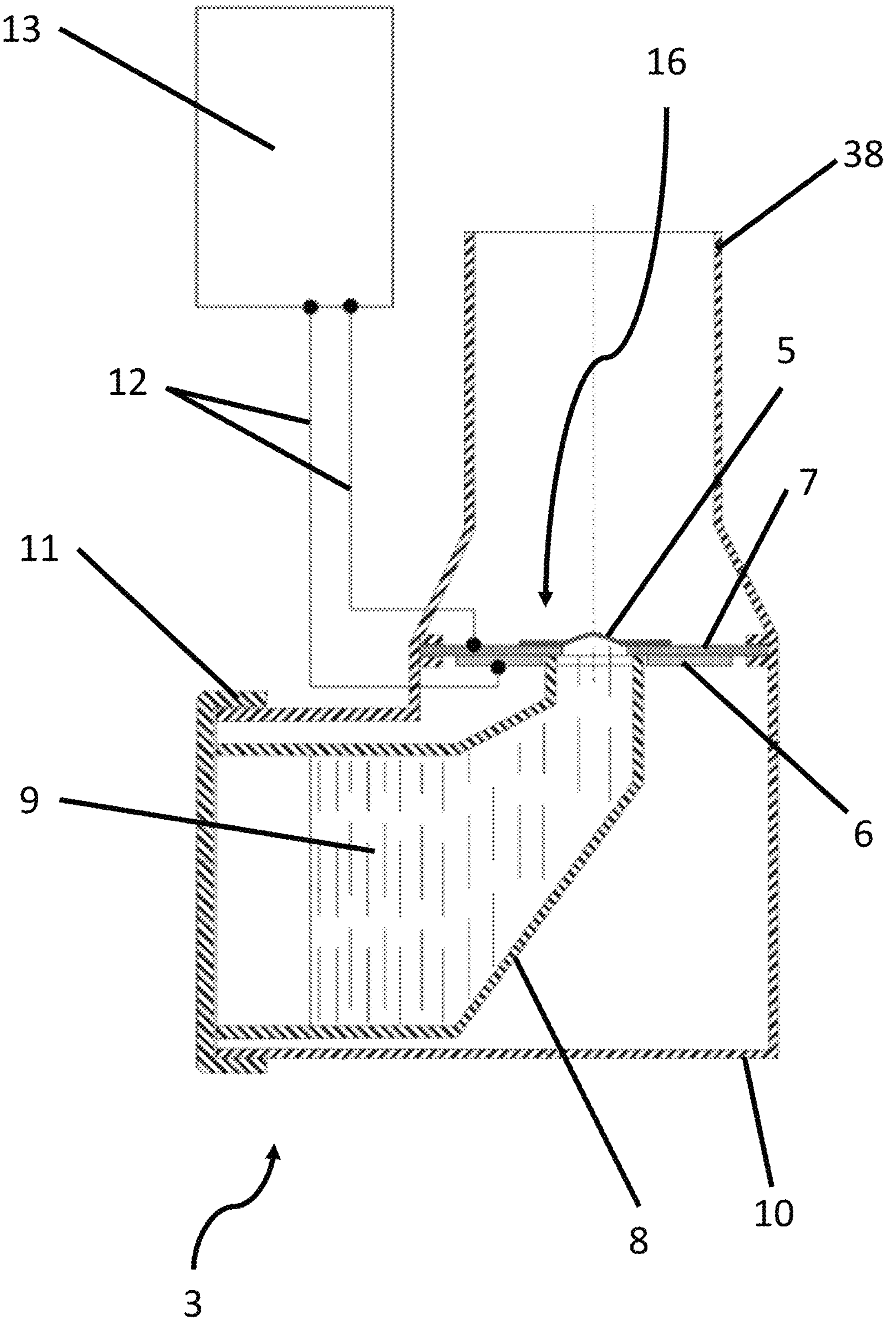
FIG. 2 schematically shows the structure of an exemplary embodiment of the nebulizer according to the invention.

FIG. 2 schematically shows the structure of an exemplary embodiment of the nebulizer 3 according to the invention. In this case, the aerosol generator 16 is arranged in a housing 10, the aerosol generator 16 consisting of a substrate plate 7, a perforated membrane 5 and a piezo element 6. By way of example, the substrate plate 7 is substantially circular and has a cutout or an opening in the center. This opening is closed off by the perforated membrane 5, the membrane 5 being connected to the substrate plate 7. The connection between the substrate plate 7 and membrane 5 can be implemented, for example, by adhesive bonding, pressing in, pressing on, welding or other suitable methods. The perforated membrane 5 is for example bulged and placed on the substrate plate 7 in such a way that the liquid 9 is guided from the back into the bulge at the membrane. Thus, the membrane 5 bulges outward from the view of the liquid 9. The piezo element 6 is likewise arranged on the substrate plate 7. By way of example, the piezo element 6 is likewise circular and has an opening in the center. By way of example, the piezo element 6 is designed such that the diameter of the opening of the piezo element 6 is greater than the diameter of the opening of the substrate plate 7 and the diameter of the substrate plate 7 is greater than the diameter of the piezo element 6. Thus, the substrate plate 7 protrudes beyond the outer edge of the piezo element 6 and also protrudes beyond the inner edge (i.e., the edge of the opening) of the piezo element 6. Thus, the substrate plate 7 protrudes beyond both edges of the piezo element 6. The substrate plate 7 and the piezo element 6 are interconnected, for example by adhesive bonding, pressing on, pressing in, welding or other suitable connecting methods.

The piezo element 6 deforms when a voltage is applied, and thereby also induces a deformation of the connected substrate plate 7. By way of example, the piezo element 6 may contract or expand when a voltage is applied, as a result of which the substrate plate 7 is bent and the membrane 5 is deflected from the rest position and, optionally, likewise slightly expanded or compressed.

A liquid reservoir 8 for storing the liquid 9 is also arranged in the housing 10. The liquid reservoir 8 is configured in such a way that the liquid 9 is guided to the membrane 5 of the aerosol generator 16 on one side. In this case, the aerosol generator 16 represents a boundary between the liquid reservoir 8 and the respiratory gas, which is guided through the tube 2 or the tee joint 4 (see FIG. 1). The liquid reservoir 8 is sealed by a lid 11 in exemplary fashion.

The nebulizer 3 is connected to the tube system or the tee joint 4 by way of a connecting piece 38, and the produced aerosol is guided into the respiratory gas and for example to a patient.

The control electronics 13 of the nebulizer 3 are connected to the aerosol generator 16 by way of electrical connections 12 in exemplary fashion. By way of example, the control electronics 13 control the aerosol production rate and production amount. Additionally, the control electronics 13 are at least configured to determine and set an optimal excitation frequency for the aerosol generator. By way of example, the resonant frequency of the aerosol generator 16, optionally in connection with other elements, can be considered to be the optimal excitation frequency. By way of example, the resonant frequency of the resonant circuit 44 may also be considered to be the optimal excitation frequency. Additionally, the amplitude of the deformation of the piezo element 6 can be controlled by way of the control electronics 13, as a result of which the aerosol production is influenced directly.

In some embodiments, the nebulizer 13 may also comprise a plurality of independently controllable aerosol generators 16. By way of example, these may have differently perforated membranes and/or be served by different liquid reservoirs 8. By way of example, this also allows a plurality of different active ingredients to be added to the respiratory gas as an aerosol independently of one another and allows these to be metered according to requirements.

Figure 3A:
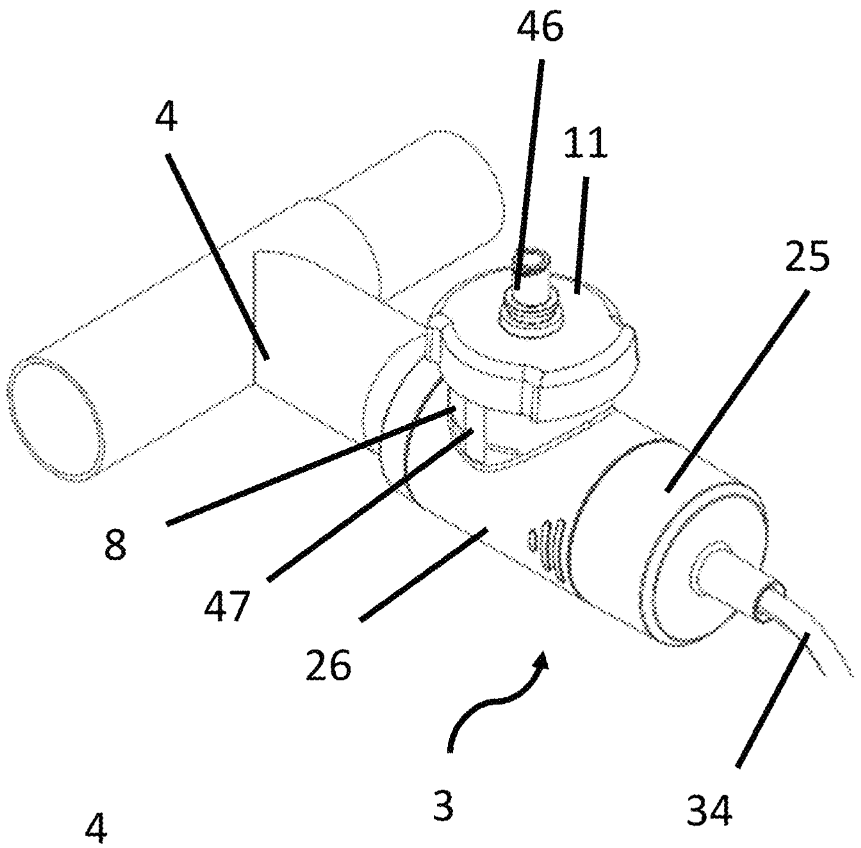
FIGS. 3A and 3B show an exemplary embodiment of a nebulizer and a tee joint in an assembled perspective view and in an exploded view, respectively.
Figure 3B:
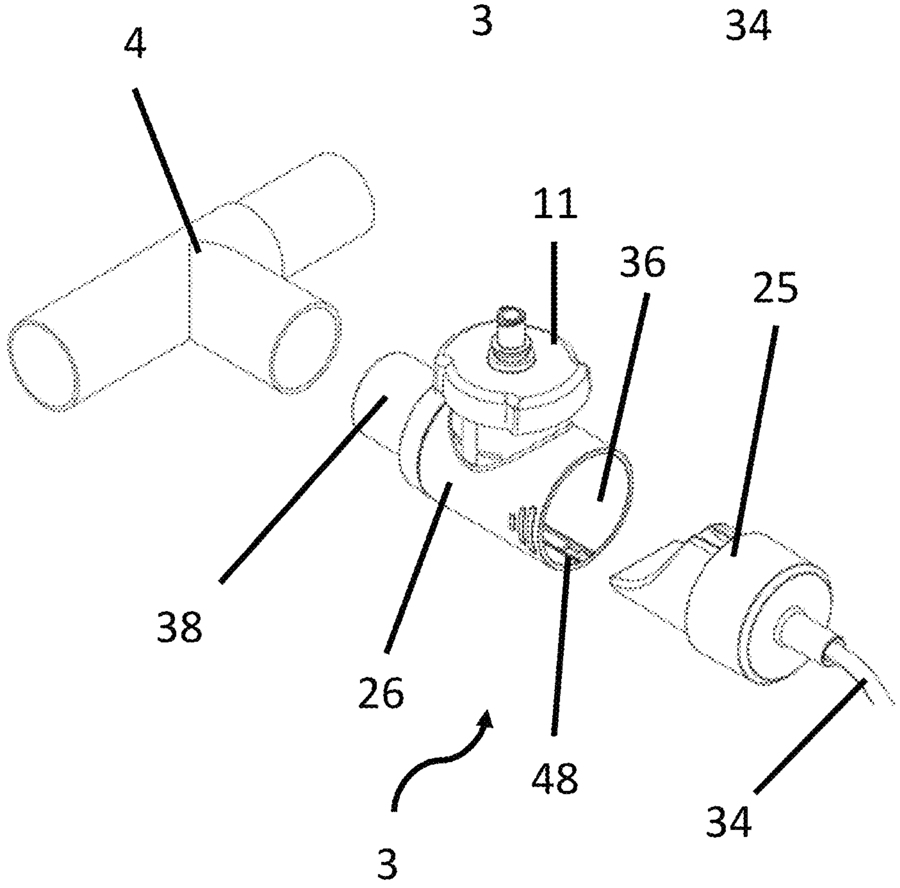

FIG. 3 shows an exemplary embodiment of the nebulizer 3 and the tee joint 4 in an assembled perspective view (FIG. 3A) and in an exploded view (FIG. 3B). In this case, the nebulizer 3 consists of two main constituents, the nebulizer part 26 and the electronics part 25. By way of example, the electronics part 25 contains the control electronics 13 of the nebulizer 3 and can be reused. The nebulizer part 26 at least comprises the aerosol generator 16 and the liquid reservoir 8. By way of example, the nebulizer part 26 can be planned as a disposable product such that the nebulizer part 26 is used for only one patient and a new nebulizer part 26 is inserted for a new patient, with the electronics part 25 also being able to be used for multiple patients. In some embodiments, the nebulizer part 26 may likewise be designed for multiple use, for example by using easy-to-clean materials and by virtue of a simple disassembly. At least part of the nebulizer part 26 can be reused in some embodiments; by way of example, the aerosol generator 16 may be exchangeable while the housing 10 including the connecting piece 38 are reused.

In the embodiment shown, a fill level indicator 47 is for example arranged on the liquid reservoir 8. By way of example, the fill level indicator 47 can be realized by an at least partly transparent wall of the liquid reservoir 8, through which the level of the liquid 9 can be seen. To this end, additional markings are also arranged in some embodiments, for example for marking a maximum and/or minimum fill level.

The liquid reservoir 8 is sealed using a lid 11. The lid 11 can be removed in order to fill and/or refill the liquid reservoir 8 with a liquid 9. Optionally, a filling device 46 may also be arranged on the lid 11, the former for example allowing the liquid 9 to be refilled during operation. Filling by the filling device 46 is also possible. By way of example, the filling device 46 can be a nozzle, in which a syringe can be placed. In some embodiments, the filling device 46 may also be a sealable opening and/or a septum, which is pierced by an injection needle and which generally seals itself again after the needle has been removed. In some embodiments, devices for pressure equalization are provided for the lid 11 (including the filling device 46) and/or the liquid reservoir 8 such that, for example, no positive pressure arises in the case of filling by way of a syringe and no liquid 9 is inadvertently pressed through the membrane 5.

By way of example, the nebulizer 3 is connected to the tee joint 4, which is gas-connected to the tube 2, by way of the connecting piece 38 on the nebulizer part 26. The produced aerosol is introduced into the respiratory gas flow via the tee joint 4 and for example supplied/guided to a patient. Preferably, the connecting piece 38 and the tee joint 4 are designed such that the aerosol production is implemented as close as possible to the respiratory gas flow so that the aerosol only travels a short distance before it can merge into the respiratory gas flow.

The nebulizer part 26 moreover comprises an insertion opening 36, into which the electronics part 25 is inserted and connected to the nebulizer part 26. By way of example, a guide rail 48 can be arranged in the interior of the nebulizer part 26 to this end, said guide rail serving inter alia for the correct insertion of the electronics part 25 by way of a guide element 49 that is complementary to the guide rail 48. In some embodiments, additional guide rails 48 and/or guide elements 49 are also arranged in the insertion opening 36, each of these having a complementary form to the corresponding elements on the electronics part 25.

By way of example, the electronics part 25 is guided into the insertion opening 36 of the nebulizer part 26 and can for example latch in there. The electronics part 25 at least comprises the control electronics 13 of the nebulizer 3. Contact between the aerosol generator 16 in the nebulizer part 26 and the control electronics 13 in the electronics part 25 is established by way of electrical lines 12. By way of example, the electronics part 25 can be connected to a ventilator 1 by way of a cable 34. By way of the ventilator 1, the nebulizer 3 can for example thus be controlled, for example within the meaning of commands relating to the time, the duration and amount of aerosol production, and/or can be supplied with power. Thus, specifications regarding the aerosol production can be entered by way of the ventilator 1, said specifications being received and implemented by the nebulizer 3 or the control electronics 13.

In some embodiments, the nebulizer 3 can be operated independently of the ventilator 1. To this end, the nebulizer 3 for example comprises its own power supply in the form of a rechargeable battery/a battery and/or a connector to the local power grid. An activation/deactivation of the nebulizer 3 is then implemented by way of the connection to a power supply and/or by a switch. It is moreover conceivable for the nebulizer 3 to comprise operating elements by means of which different options, for example the amount of aerosol to be produced, can be set. Communication between the nebulizer 3 and the ventilator 1 by radio is also possible in some embodiments.

The embodiment of the nebulizer 3 shown in FIG. 3 is in two parts, consisting of an electronics part 25 and a nebulizer part 26, which can be separated from one another. In some embodiments, the nebulizer 3 is also formed in one part. So that the nebulizer 3 can be reused, at least an exchangeable and/or removable aerosol generator 16 would be considered in this case.

Figure 4A:
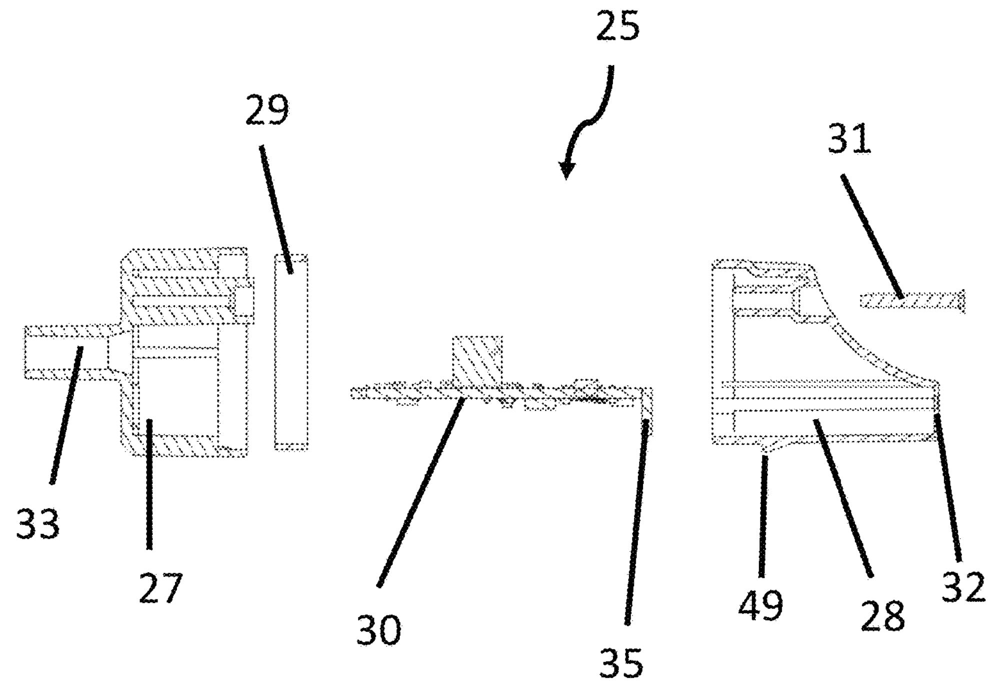
FIGS. 4A and 4B show an exemplary embodiment of an electronics part as section view and as a perspective view.
Figure 4B:
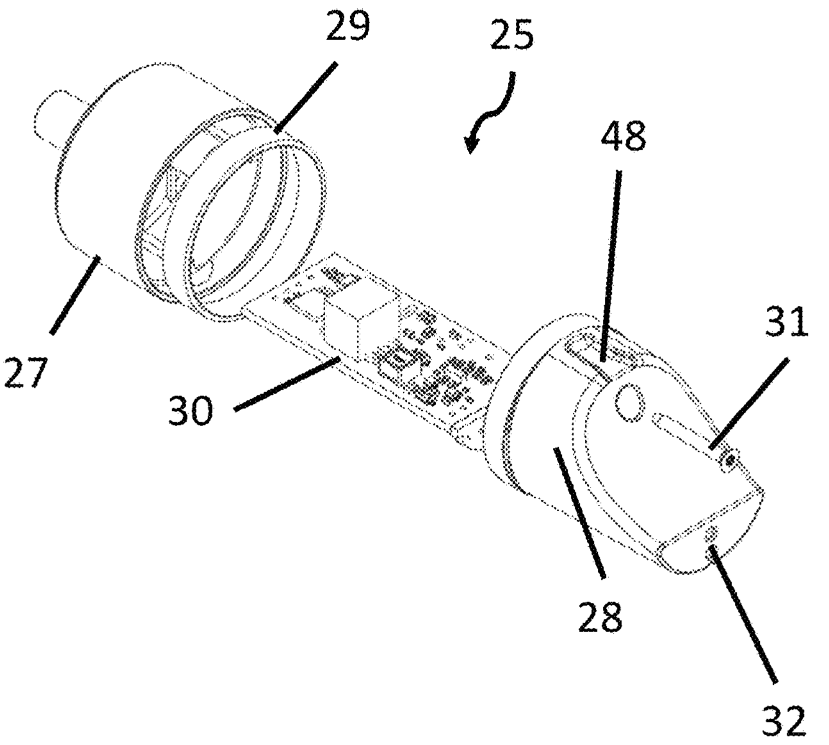

An exemplary embodiment of the electronics part 25 is depicted in an exploded view in FIG. 4. FIG. 4A shows a section through the electronics part 25 and FIG. 4B shows a perspective view.

By way of example, the electronics part 25 is composed of two housing parts 27, 28, in which, amongst others, the printed circuit board 30 with the control electronics 13 is arranged. The two housing parts 27, 28 are inter alia affixed to one another by way of a screw 31. As an alternative or in addition, the housing parts 27, 28 can also be affixed by way of a plug-in and/or clamping and/or latching connection. In the exemplary embodiment, the housing part 28 is at least partly plugged into the housing part 27. For additional sealing, for example against moisture and/or liquids, an O-ring 29 is arranged between the housing parts 27, 28.

The housing part 27 comprises a cable connector 33, by means of which the cable 34 can be connected to the printed circuit board 30. By way of example, the cable connector 33 can be designed as a leadthrough such that cable 34 can be pushed, at least in part, through the leadthrough. The cable 34 and/or the cable connector 33 are optionally designed such that the cable connector 34 is sealed against the ingress of moisture and/or liquid into the electronics part 25. By way of example, when embodied as a leadthrough, the cable connector 34 slightly tapers conically such that the cable 33 is sealingly clamped when led through. In some embodiments the housing part 27 contains elements to which the printed circuit board 30 can be fastened. By way of example, the printed circuit board 30 can be affixed in the housing part 27 by way of screw-in connections. Alternatively or in addition, plug-in elements are provided for the printed circuit board 30 in some embodiments. In some embodiments the printed circuit board 30 comprises plug-in connections for the cable 34. Thus, the cable 34 can be connected, for example detachably connected, to the electronics part 25. By contrast, some embodiments may provide for the cable 34 to be securely connected to the electronics part 25, that is to say to the printed circuit board 30 and/or housing part 27.

The printed circuit board 30 at least comprises the control electronics 13 of the nebulizer 3. In the case of a connection by way of a cable 34, there is additionally at least the provision of further elements by means of which the lines of the cable 34 are connected to the printed circuit board 30. Further, at least one contact element 35, by means of which the contact is established between the printed circuit board 30 and the aerosol generator 16, is arranged on the printed circuit board 30. The contact element 35 additionally comprises at least one sealing element, for example a rubber seal.

By way of example, contact with the aerosol generator 16 is implemented by way of openings 32 that are formed in the housing part 28. By way of example, the electrical connections 12 are connected to the contact element 35 via the openings 32. In the region of the openings 32, the interior of the electronics part 25 is sealed against moisture and/or the ingress of liquid by way of the sealing elements at the contact element 35. Alternatively or in addition, sealing elements, e.g., rubber seals, are arranged on and/or in the openings 32 in some embodiments in order to seal against the ingress of moisture and/or liquid. By way of example, the openings 32 have a rubber leadthrough, which seals around the electrical connections 12.

Optionally, apparatuses for holding the printed circuit board 30 are also arranged in the housing part 28. By way of example, screwing points and/or plug-in elements can be provided to this end. In some embodiments, the region of the housing part 28 in which the contact element 35 of the printed circuit board 30 is arranged is designed such that the contact element 35 is slightly jammed.

By way of example, the housing part 28 comprises a guide rail 48 and a guide element 49. By way of example, the guide rail 48 is designed so as to be complementary to a guide element in the insertion opening 36 of the nebulizer part 26. Firstly, the guide element 49 is designed such that it is guided in the guide rail 48 of the nebulizer part 26; secondly, the guide element 49 can also latch in the guide rail 48 of the nebulizer part 26 in at least one position. By way of example, this can produce feedback that the nebulizer part 26 and electronics part 25 are correctly plugged together.

Figure 5:
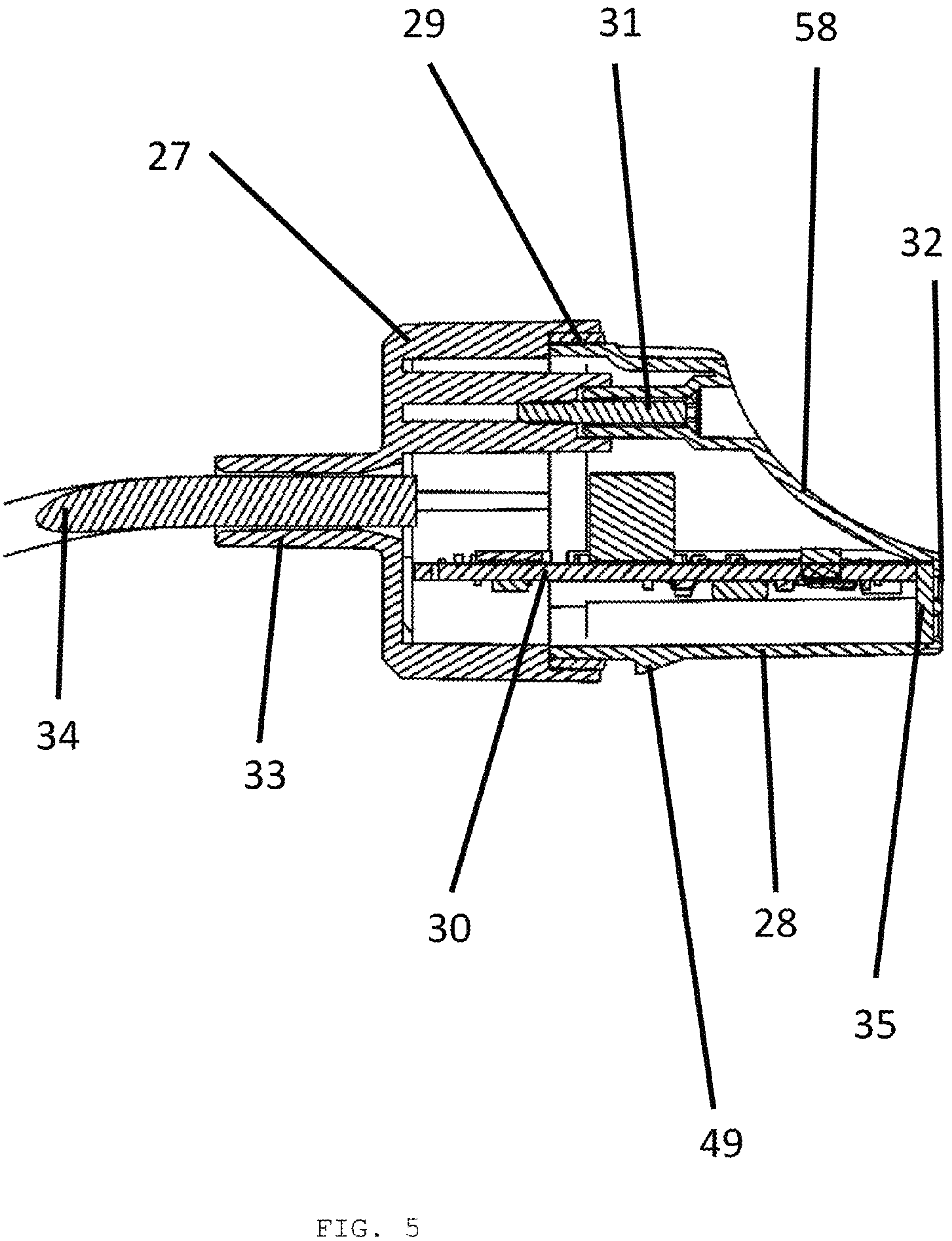
FIG. 5 shows a section of an assembled form of an exemplary electronics part.

FIG. 5 depicts a section of an assembled form of the electronics part 26 in exemplary fashion. The housing part 27 is affixed to the housing part 28 by way of the screw 31. An O-ring 29 is arranged between the housing parts 27, 28 in the region where the housing part 28 is partly inserted into the housing part 27.

The printed circuit board 30 is arranged in such a way that the contact element 35 is arranged in the region of the openings 32 of the housing part 28. Specifically, the contact element 35 has been placed in such a way that an electrical connection 12 to the aerosol generator 16 of the nebulizer part 26 can be established through the openings 32. Sealing elements which seal the interior of the electronics part 25 against an ingress of moisture and/or liquid through the openings 32 are arranged in the region of the contact element 35 and/or in and/or on the openings 32.

The cable 34 is connected to the electronics part 25 by way of the cable connector 33. In this case, the cable 34 has been inserted into the leadthrough of the cable connector 33 so that there is a seal here against the ingress of liquid and/or moisture.

By way of example, the housing part 28 has an arcuate section 58, which is characterized in that the housing wall runs in an arc in this region. In some embodiments, this arcuate section 58 is adjusted to match the wall 59 of the nebulizer part 26 (see FIG. 7), that is to say it may also run obliquely and/or, at least in sections, straight instead of having the arcuate form. If arcuate section 58 and wall 59 are matched to one another and run in arcuate fashion, both for example have corresponding radii.

Figure 6:
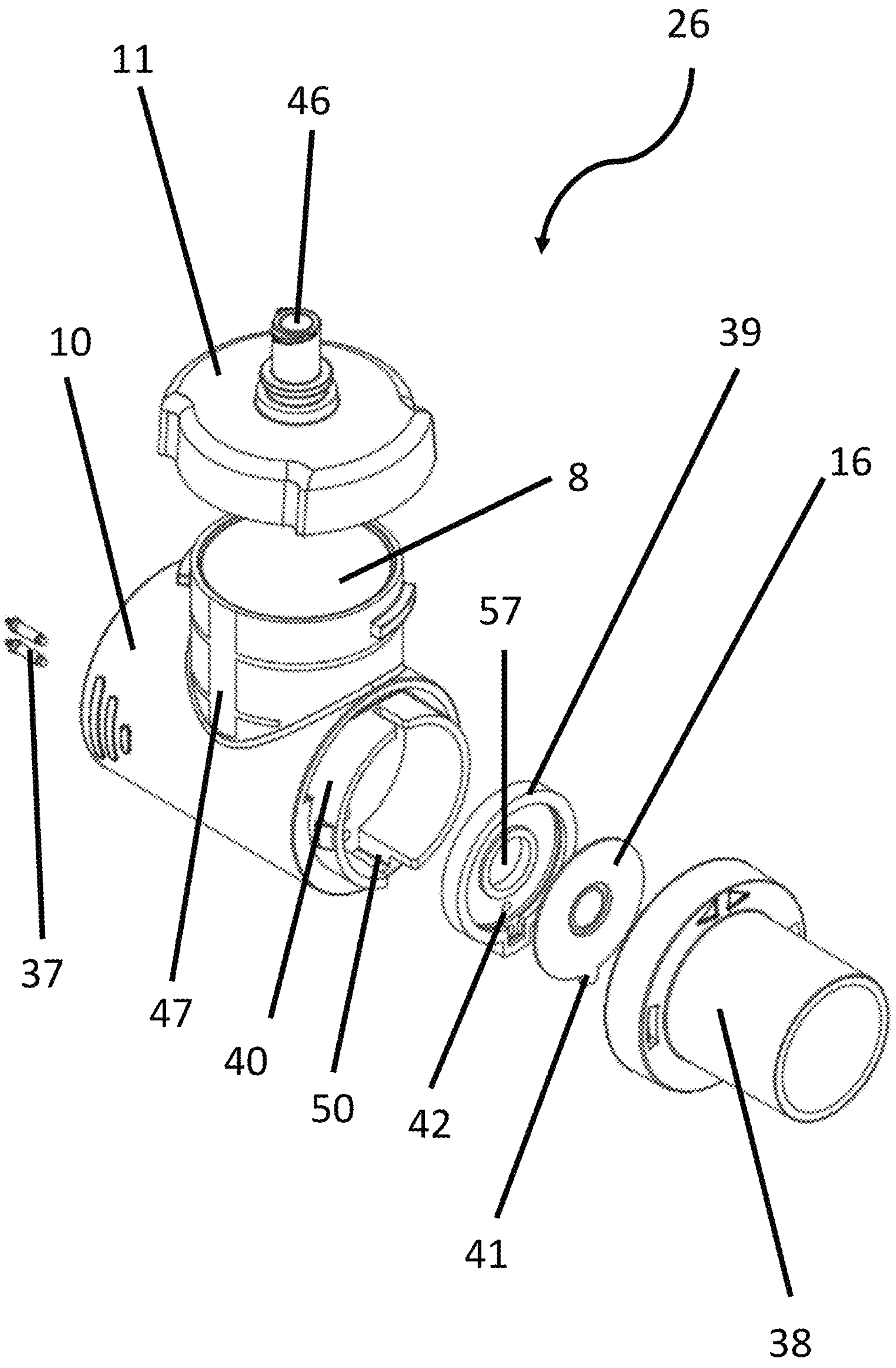
FIG. 6 shows a perspective exploded view of an exemplary embodiment of a nebulizer part.

An exemplary embodiment of the nebulizer part 26 is depicted in a perspective exploded view in FIG. 6. By way of example, the nebulizer part 26 comprises inter alia a housing 10 with the liquid reservoir 8, which can be sealed by way of a lid 11. Additionally, the nebulizer part 26 comprises the aerosol generator 16 which is mounted in a frame 39 in the housing 10, and a connecting piece 38 which is connected to the housing 10 via a connector receptacle 40 and which fixates the frame 39 with the aerosol generator 16 in the housing 10. By way of example, the frame 39 with the aerosol generator 16 is pushed up to the boundary 54 (see FIG. 7). To this end, a guide groove 50 is formed in the housing 10 of the nebulizer part 26, for example. The connecting piece 38, for example in the form of a flange, is placed thereover or plugged onto the connector receptacle 40 and for example fixated by way of a bayonet closure and/or a simple plug-in connection. By way of example, latching grooves and/or other latching elements may be arranged on the connecting piece 38, which latch into complementary latching elements of the connector receptacle 40. The connecting piece 38, the frame 39 with aerosol generator 16 and the boundary 56 and the connector receptacle 40 of the housing 10 are dimensioned in such a way here that the frame 39 with the aerosol generator 16 is fixated by the connecting piece 38.

The frame 39 for the aerosol generator 16 has at least one opening 57, by means of which the liquid 9 is led from the liquid reservoir 8 to the perforated membrane 5 of the aerosol generator 16. Moreover, the frame has at least one opening 42, through which the contact pins 37 can be plugged in order to establish an electrical connection 12 between the aerosol generator 16 (via the electronics contact 41) and the contact element 35 of the printed circuit board 30. Corresponding complementary openings are likewise arranged in the boundary 54.

The lid 11 comprises a filling device 46 in exemplary fashion, by means of which liquid 9 can be (re-)filled into the liquid reservoir, for example during operation. By way of example, the liquid reservoir 8 comprises a fill level indicator 47, by means of which the fill level of the liquid 9 can be monitored when necessary. In the embodiment shown, the lid 11 is detachably connected to the housing 10, for example by way of a bayonet closure. In some embodiments, other closure options for the lid 11 are also conceivable as an alternative or in addition thereto.

Figure 7:
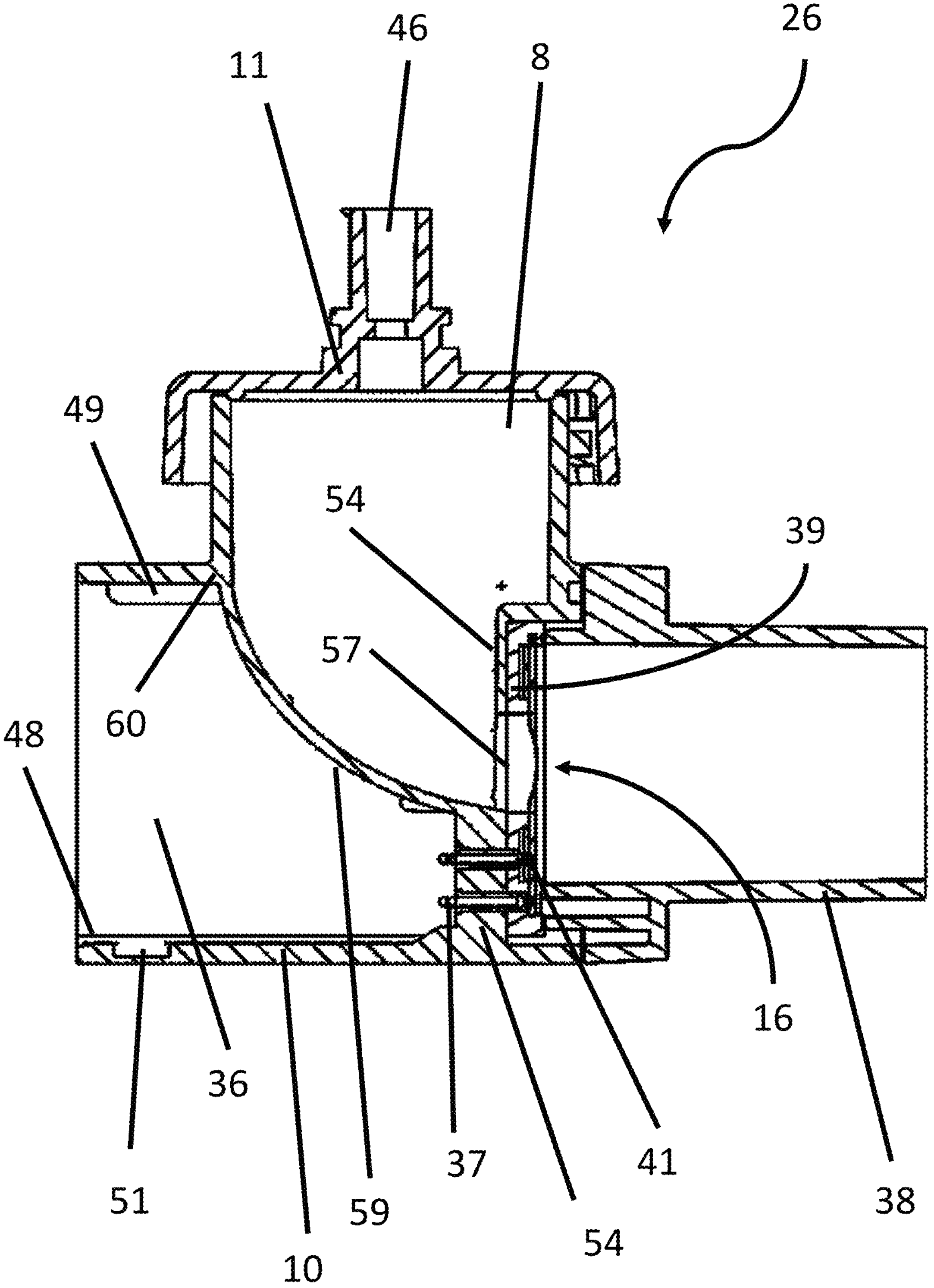
FIG. 7 shows an aerosol generator of a nebulizer mounted in a frame of a housing.

A section through an exemplary embodiment of the nebulizer part 26 is depicted in FIG. 7. A wall 59 separates the liquid reservoir 8 from the insertion opening 36 for the electronics part 25. Leadthroughs are formed within the boundary 54 so that an electrical connection 12 can be established between the electronics contact 41 of the aerosol generator 16 and the contact element 35 of the printed circuit board 30 by way of the contact pins 37. The aerosol generator 16 is a mounted in the frame 39 in the housing 10 of the nebulizer part 26. The frame 39 with the aerosol generator 16 is held by the connecting piece 38, which presses the frame 39 against the boundary 54. The frame 39 and/or the boundary 54 optionally comprise sealing elements such that no liquid 9 from the liquid reservoir 8 inadvertently enters into the connecting piece 38. An additional O-ring is arranged between the frame 39 and the boundary 54 and/or between the frame 39 or the aerosol generator 16 and the connecting piece 38 in some embodiments. In some embodiments, the electronics contact 41 and/or the leadthrough 42, in particular, are designed such that no moisture and/or liquid enters into the insertion opening 36 or reaches the electronics part 25. In some embodiments, to this end the region of the electronics contact 41 of the aerosol generator 16, in particular, is sealed accordingly.

At least one guide rail 48 with a complementary embodiment to the guide element 49 of the electronics part 25 is arranged in the insertion opening 36. Moreover, at least one latching position 51, into which the guide element 49 of the electronics part 25 can latch, is formed in the guide rail 48. Additionally, a guide element 49 is also formed within the insertion opening 36 of the nebulizer part 26, fitting to the guide rail 48 of the electronics part 25.

By way of example, the wall 59 between the insertion opening 36 and the liquid reservoir 8 is bent. In this case, the profile of the wall 59 for example corresponds to the arcuate section 58 of the housing part 28 of the electronics part 25. Inter alia, a simplified, correctly oriented insertion of the electronics part 25 into the insertion opening 36 of the nebulizer part 26 can be achieved as a result.

Here, the profile of the wall 59 is also such that it terminates with the edge of the opening 57 above the leadthrough 42 for the contact pins 37. By way of example, the edge of the opening 57 and the wall 59 form a surface. What the bent shape of the wall 59 in combination with the end level with the edge of the opening 57 facilitates is that, firstly, there is only a small dead volume of liquid that cannot be nebulized to form an aerosol as it does not reach the membrane 5 of the aerosol generator 16. Secondly, this also prevents the possibility of liquid remains being deposited in possible corners, and likewise being unable to be consumed. In some embodiments the wall 59 is not bent but runs in a straight line from the corner 60 to the opening 57. In particular, the wall 59 is designed such that the liquid 9 in the liquid reservoir 8 is led to the aerosol generator 16 or the membrane 5.

Figure 8A:
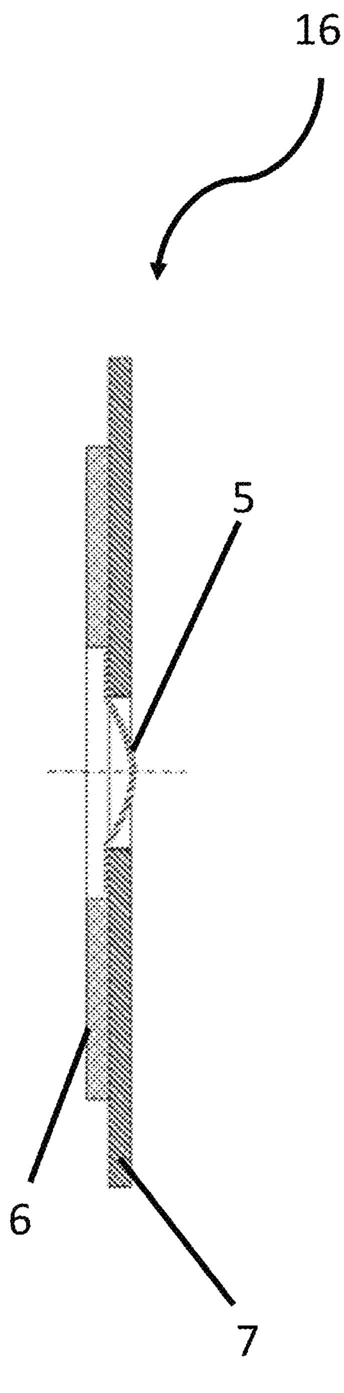
FIGS. 8A-8C schematically show a section of an exemplary embodiment of an aerosol generator in the rest state and in two operating states.
Figure 8B:
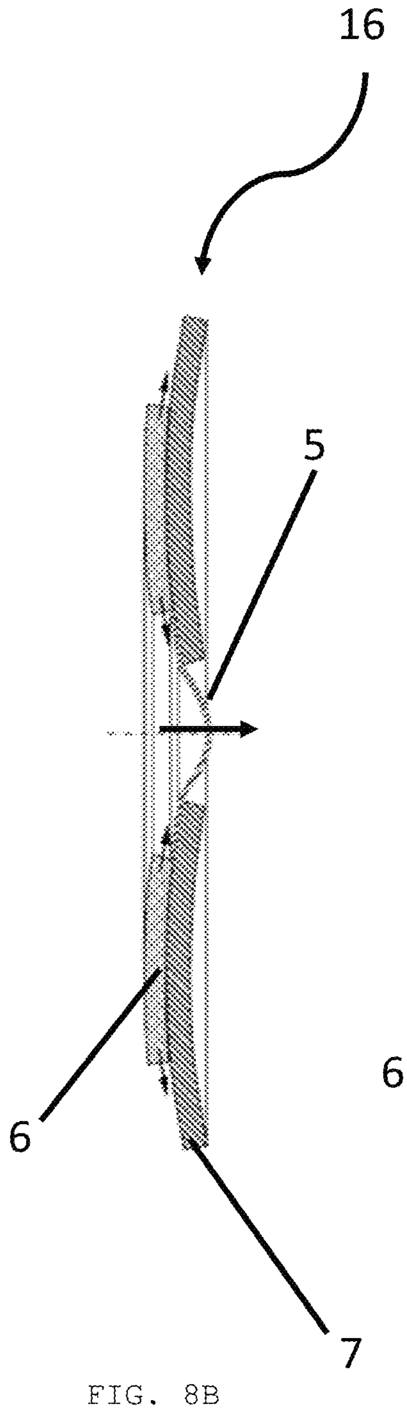
Figure 8C:
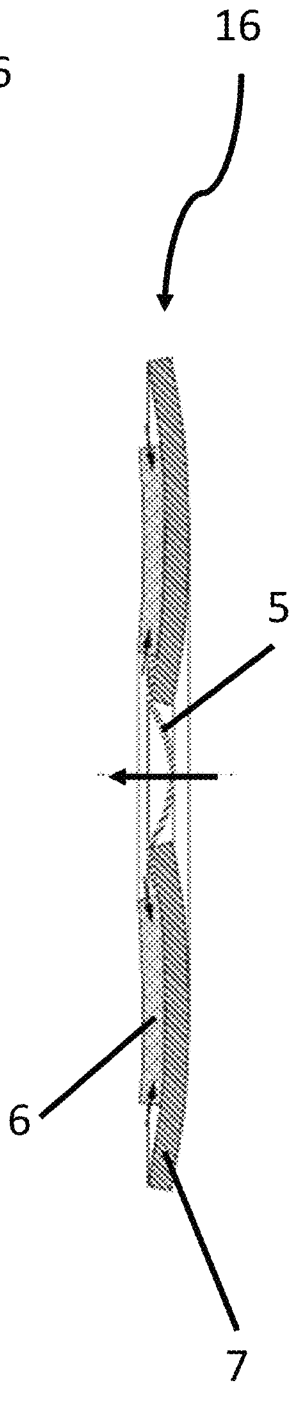

FIG. 8 schematically depicts a section of an exemplary embodiment of the aerosol generator 16 in the rest state (FIG. 8A) and in two operating states (FIGS. 8B and 8C).

The rest state, that is to say when no voltage is applied or else when an applied AC voltage passes through zero, the piezo element 6 is in a non-deformed state. By way of example, the piezo element 6 and the substrate plate 7 are designed such that these each form a plane in a non-deformed state. In particular, both the piezo element 6 and the substrate plate 7 are designed as a plate and each have a central opening. The piezo element 6 and the substrate plate 7 are interconnected such that these cannot move independently of one another. By way of example, the piezo element 6 is securely connected to the substrate plate 7 on one side. In some embodiments, both the piezo element 6 and the substrate plate 7 have a circular form, with the opening being formed centrally in each case. By way of example, the substrate plate 7 and the piezo element are arranged centrally above one another such that the centers of the surfaces are overlaid. By way of example, the piezo element 6 is designed as a piezo actuator.

Moreover, the perforated membrane 5 is also securely connected to the substrate plate 7. The membrane 5 is slightly arched in the embodiment shown in exemplary fashion. The membrane 5 is arranged such that the latter closes the opening in the substrate plate 7 and/or piezo element 6. In some embodiments, the membrane 5 is arranged so that the arching projects into and/or projects through the opening of the substrate plate 7. In the embodiment shown in exemplary fashion, the membrane 5 is connected to the substrate plate 7 on the same side as on which the piezo element 6 is also connected to the substrate plate. If the membrane 5 has an arched embodiment, the membrane 5 is generally arranged in such a way that the arching points away from the liquid 9 in the liquid reservoir 8. Thus, the liquid 9 may flow into the arch. In some embodiments, the membrane 5 may also be arranged on the side of the substrate plate 7 that is opposite to the side with the piezo element 6. In this case, the arch of the membrane 5 would not project into the opening of the substrate plate 7.

The membrane 5 is preferably perforated, that is to say has at least one small opening 14 through which the liquid 9 can be pressed at least intermittently in order to produce an aerosol. In this case, the droplets tear off from the side of the membrane 5 facing away from the liquid 9. The membrane 5 preferably has a plurality of openings 14 in the form of a perforation. The openings 14 in the membrane 5 are preferably circular but may by all means also deviate therefrom. By way of example, the openings 14 have a diameter between 0.1 μm and 300 μm (0.3 mm), with the diameter being able to be chosen depending on the desired average droplet size of the aerosol. The larger the desired droplet size of the aerosol is designed to be, the larger it is for example also possible to choose the openings 14. At this point, reference is made to the fact that further factors such as the viscosity of the liquid 9, for example, may also have an influence on the droplet size.

The openings 14 in the membrane 5 taper conically in some embodiments. By way of example, the openings 14 in the membrane 5 have a greater diameter on the side on which the liquid 9 is led thereto than on the side on which the liquid 9 tears from the membrane 5 as aerosol droplets.

In particular, the openings 14 are dimensioned such that substantially no liquid 9 from the liquid reservoir 8 passes through the membrane 5 in the rest state, that is to say at times in which no aerosol should be produced. It should be noted in this context that the deformation of the aerosol generator 16 inter alia passes through the state depicted in FIG. 8A during operation, that is to say when aerosol should be generated, and, unlike in the rest state, liquid 9, for example in the form of the smallest droplets or aerosol droplets, can by all means also pass through the membrane 5.

The piezo element 6 deforms when a voltage is applied, as indicated in FIGS. 8B and 8C. In this case, opposite voltages are applied between the states shown in FIGS. 8B and 8C (e.g., a positive voltage in 8B and a negative voltage in 8C, or vice versa).

In the representation shown in FIG. 8B, a deformation of the piezo element 6 is induced by the application of a voltage to said piezo element 6. In this case, the piezo element 6 expands laterally, as indicated by the arrows at the piezo element 6 in FIG. 8B. As a result of the piezo element 6 being securely connected to the substrate plate 7, the deformation induced in the piezo element 6 is transferred to the substrate plate 7, leading to said substrate plate 7 bending. As a result of the substrate plate 7 bending, the membrane 5 is also deflected at the same time, as elucidated by the arrow at the membrane 5 in FIG. 8B. In the process, the liquid 9 queuing at the membrane 5 follows.

If the voltage at the piezo element 6 is reduced again, the piezo element 6 contracts again or the expansion reduces, with the substrate plate 7 and the membrane 5 following the movement accordingly. When an opposite voltage is applied to the piezo element 6, the piezo element 6 contracts, as elucidated by the arrows at the piezo element 6 in FIG. 8C. As a result, the substrate plate 7 is likewise deformed and simultaneously deflects the membrane 5 (cf., arrow in FIG. 8C).

The entire system is excited to vibrate by the application of an AC voltage, that is to say it alternates periodically between the extremal states in accordance with FIGS. 8B and 8C. The aerosol generator 16 is ideally operated with an excitation frequency of the AC voltage which corresponds to the resonant frequency and/or a multiple of the resonant frequency of the aerosol generator 16.

Figure 9:
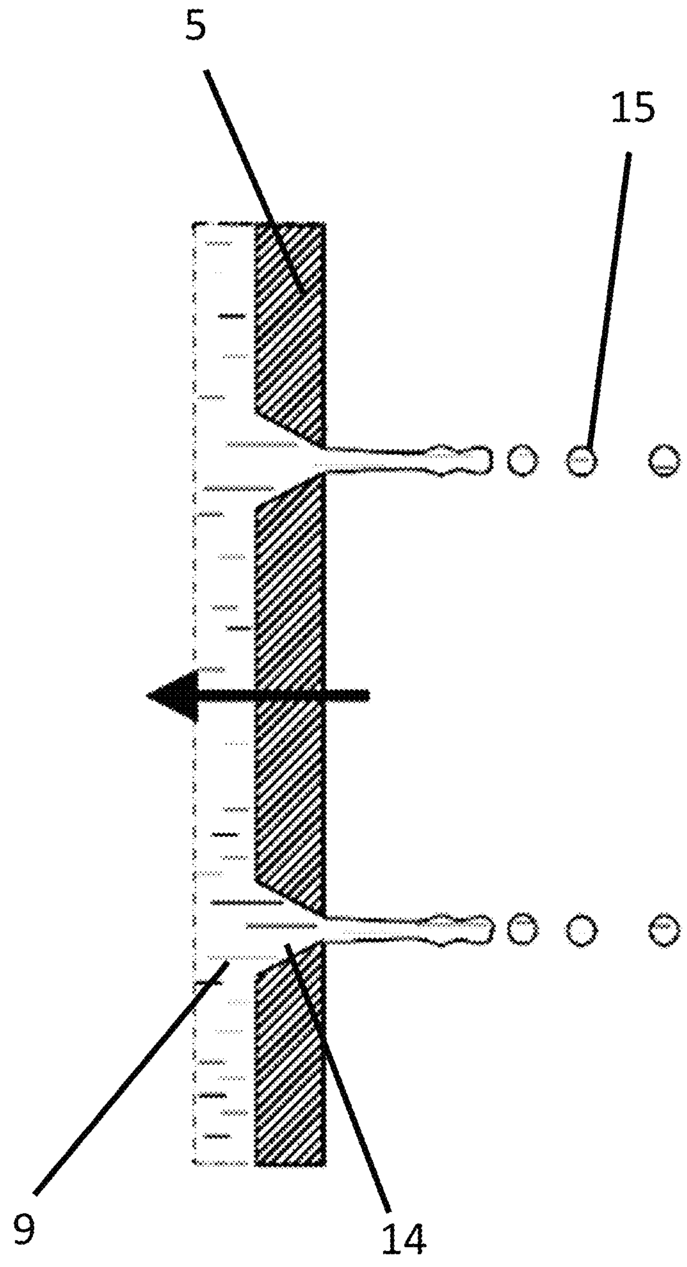
FIG. 9 shows an exemplary aerosol production.

The aerosol production is depicted in exemplary fashion in FIG. 9. If the membrane 5 moves from the extremal position of FIG. 8B in the direction of the extremal position of FIG. 8C, the membrane 5 presses against the liquid 9, as depicted in FIG. 9. In this case, the arrow in FIG. 9 describes the movement direction of the membrane 5. As a result of the membrane 5 being pressed against the liquid 9 the liquid 9 is at least partly pressed through the openings 14. In this case, the liquid 9 tears off, into aerosol droplets 15, from the side of the membrane 5 facing away from the liquid 9. The size of the aerosol droplets is determined, inter alia, by the diameter of the openings 14 on the side of the membrane 5 facing away from the liquid 9.

In this case, the deformation of the piezo element 6 is dependent on the applied voltage in particular. Within certain boundaries, what applies in principle is that a higher voltage leads to greater deformation. Thus, if the aerosol generator is operated with an AC voltage at a higher voltage, the extremal positions are spaced further apart and a greater amount of aerosol is produced. Thus, the amount of aerosol produced can be adjusted by adjusting the voltage. In this case, an increase in the voltage leads to a greater deflection of the membrane 5, and hence to a greater aerosol production rate. The aerosol production rate does not increase above a certain voltage despite the greater deflection of the membrane 5. Moreover, mechanical damage may occur at too high voltages in some embodiments.

Ideally, the aerosol generator 16 is excited by a sinusoidal function with an (excitation) frequency that corresponds to the resonant frequency of the aerosol generator 16 or the resonant circuit 44. In some embodiments, the aerosol generator 16 may also be operated at an (excitation) frequency that deviates from the resonant frequency. In some embodiments, the system or the control electronics is/are configured to automatically track the resonant frequency, for example if the latter changes as the liquid 9 is consumed.

Figure 10:
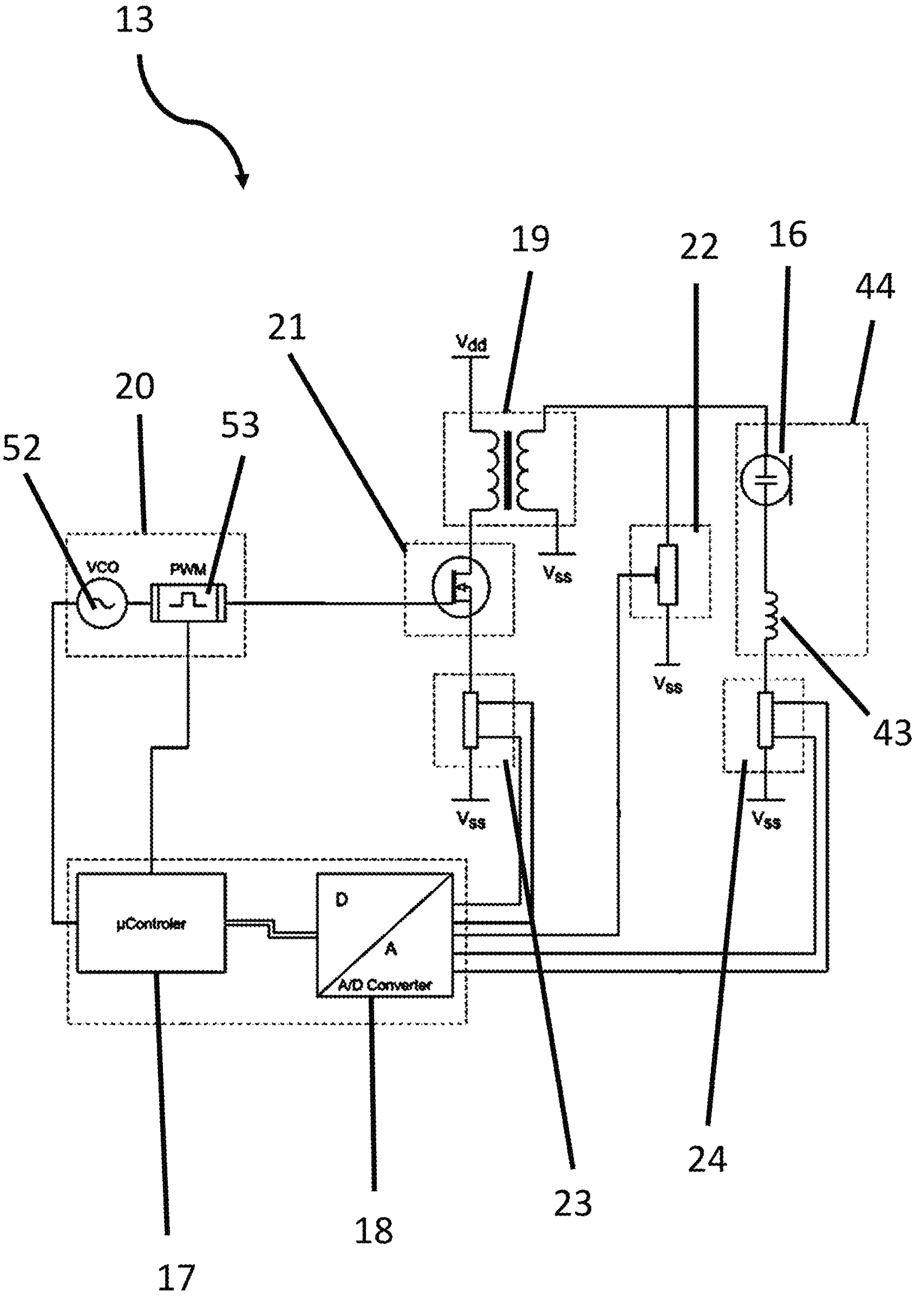
FIG. 10 shows exemplary control electronics for generating the signal with which an aerosol generator is operated.

The control electronics 13 for generating the signal with which the aerosol generator 16 is operated are depicted in exemplary fashion in FIG. 10.

In this case, the aerosol generator 16 forms a series resonant circuit 44 with a series-connected inductor 43. In this case, the resonant circuit 44 is distinguished in that the latter has a minimum volume resistance when the electromechanical system, for example consisting of aerosol generator 16 and inductor 43, is excited or operated at the resonant frequency. At the same time, a voltage rise arises at the inductor 43, for example a coil, and the aerosol generator 16. By way of example, the voltage rise can be exploited to attain an increased efficiency of the aerosol generator.

By way of example, the aerosol generator 16 can be driven with an excitation frequency of from about 1 kHz to about 200 kHz. A higher excitation frequency of up to about 500 kHz may also be used in some embodiments. In some embodiments, the aerosol generator 16 is operated at a resonant frequency.

By way of example, the operating voltage of the aerosol generator 16 is approximately 80 Vss. The operating voltage is set in the control electronics 13 by memory and switching elements. In the embodiment illustrated, the operating voltage is set by a transformer 19 in conjunction with a transistor 21. By way of example, the utilized transistor is a field effect transistor, preferably a metal oxide semiconductor field effect transistor (MOSFET). Alternatively or in addition, it is also possible to obtain a corresponding setting of the operating voltage by way of other components, for example by way of a circuit of inductors.

In this case, the resonant frequency is set by way of the radiofrequency generator (RF generator) 20. In this case, the RF generator 20 at least comprises an oscillator 52, for example a voltage-controlled oscillator (VCO), and a pulse width modulator (PWM) 53. In this case, the RF generator 20 is driven by way of a microcontroller 17 with a digital-to-analog converter (A/D converter) 18, the latter optionally being integrated. Alternatively or in addition, the pulse width modulator 53 may also be part of the microcontroller 17.

The resonant frequency is determined by way of the voltage measurement using a voltmeter 24 at the aerosol generator 16. To this end, different excitation frequencies are specified at the aerosol generator 16 and/or the resonant circuit 44, and the voltage is measured simultaneously at the voltmeter 24. The resonant frequency is at the excitation frequency for which the highest voltage can be measured. In some embodiments, the control electronics 13 are designed to automatically determine the resonant frequency. By way of example, the resonant frequency of the aerosol generator 16 and/or resonant circuit 44 also depends on the fill level of the liquid 9 in the liquid reservoir 8. There can also be a dependence of the resonant frequency on the physical properties of the liquid 9. The resonant frequency may change when liquid 9 is consumed. In some embodiments, the control electronics 13 are likewise configured to recognize changes in the resonant frequency and drive a corresponding change in the specified frequency. By way of example, a deviation from the resonant frequency can be recognized by virtue of the voltage measured by the voltmeter 24 reducing.

It is possible to determine the resonant frequency of an aerosol generator 16 in a frequency range by virtue of the voltage at the aerosol generator 16 being measured (voltmeter 24). If the excitation frequency is changed through the given frequency range, the frequency with the highest voltage at the aerosol generator 16 is the resonant frequency. The voltage drops significantly if the excitation frequency overshoots the resonant frequency.

In some embodiments, the resonant frequency can be verified during operation, for example by varying the specified excitation frequency about the resonant frequency. Thus, for example, a range of up to 1 kHz about the resonant frequency is regularly tested and the respective voltage value at the voltmeter 24 is determined. By way of example, the excitation frequency at which the highest voltage value is determined is interpreted as the (new) resonant frequency and specified for the aerosol generator 16.

In addition to the voltage measurement by way of the voltmeter 24, the current is also measured at the primary side (ammeter 23) and at the secondary side (ammeter 22) of the transformer 19 in some embodiments. By way of example, a statement about the efficiency of the operation can be made by measuring the current, and an operation at optimal efficiency can be set. If the current intensity is measured both on the primary side and on the secondary side of the transformer 19, it is possible to determine the voltage with the maximum efficiency of the circuit by changing the pulse width 60 of the RF signal 56. The efficiency arises from the ratio of primary power to secondary power. In some embodiments, the control electronics 13 are designed and configured such that the optimal efficiency is determined and set automatically.

By way of example, the amplitude of the excitation signal 55 can be set by the RF generator 20, in particular by specifying a pulse width by way of the pulse width modulator 53. The efficiency and/or the amount of aerosol produced can be increased up to a certain point by way of a greater pulse width of the RF signal 56. In some embodiments, the transformer core saturates at 50% and/or greater pulse width, for example, as a result of which the efficiency deteriorates. Additionally, an excitation signal that is too intense, for example as a result of a large pulse width, may lead to damage to the membrane 5 and/or the substrate plate 7 and/or the piezo element 6. In some embodiments, the maximum aerosol generation with simultaneously optimum efficiency is achieved at approximately 30% (+/−5%) pulse width. The pulse width relates for example to the period of a sine wave, that is to say 50% pulse width should be equated to half a period of the sine wave.

Figure 11A:
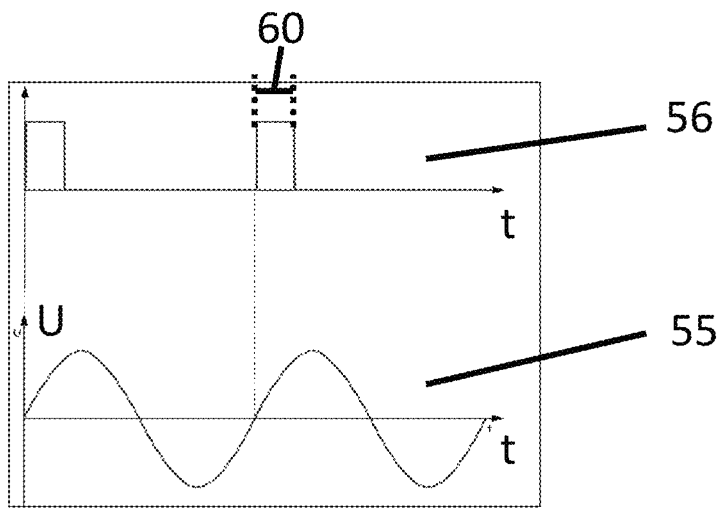
FIGS. 11A-11C represent, in exemplary fashion, rectangular RF signals and the excitation signals resultant therefrom.
Figure 11B:
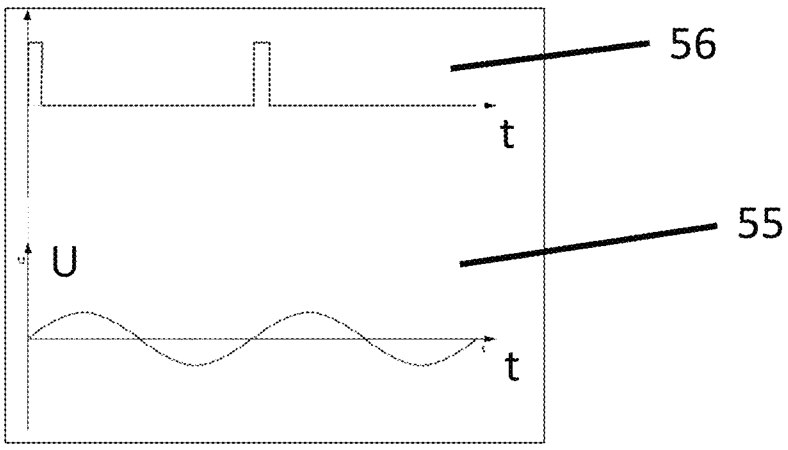
Figure 11C:
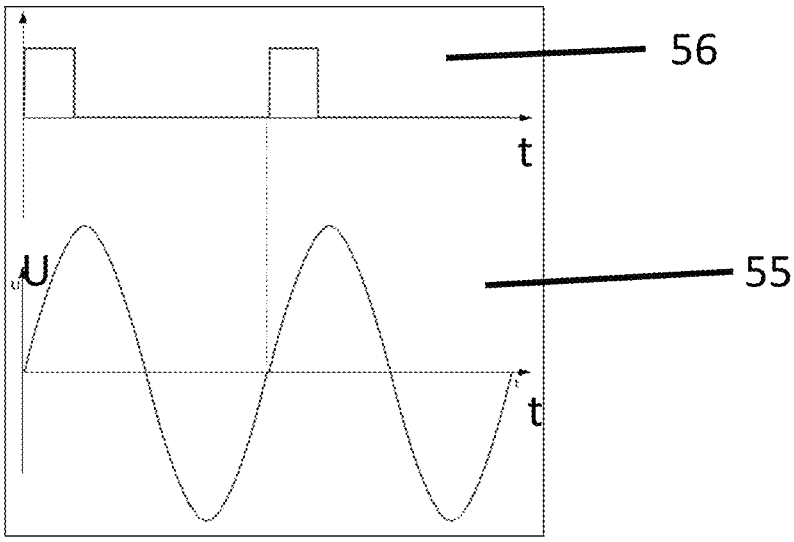

FIGS. 11A to 11C represent, in exemplary fashion, the rectangular RF signals 56 and the excitation signals 55 resultant therefrom. By way of example, the rectangular RF signal 56 with the pulse width 60 is produced by the RF generator 20. By way of this RF signal 56, the excitation signal 55 is produced by the transistor 21, the transformer 19 and the resonant circuit 44.

Shorter pulse widths 60, that is to say shorter rectangular signals, in this case produce an excitation signal 55 with a lower amplitude at the same frequency, as depicted in FIG. 11B. In this case, a lower amplitude leads, inter alia, to less aerosol production.

If larger pulse widths 60 are produced, this also increases the amplitude of the excitation signal 55, with the frequency likewise remaining unchanged. As a rule, a higher amplitude also leads to a greater aerosol production by the aerosol generator 16.

In some embodiments, the transformer core saturates at pulse widths 60 above approximately 50%. This leads to a deterioration in the efficiency of the aerosol production. In some embodiments, it is also possible for the transformer core to only saturate at pulse widths 60 above about 50%, for example above about 60% and higher. In this case, the pulse width relates to a period of the sinusoidal vibration. Thus, for example, a pulse width 60 of 50% corresponds to half a period of the sinusoidal vibration.

A maximum aerosol production with an optimal efficiency is reached at a pulse width 60 of approximately 30% (+/−5%) in some embodiments.

The aerosol generation, in particular the amount of aerosol produced, can be controlled by a modulation of the pulse width 60. By way of example, if a small amount of produced aerosol is required at a particular time, it is possible to specify a small pulse width 60 by the RF generator 20. The amount of aerosol to be produced is specified for example by the ventilator 1 in some embodiments, with the control electronics 13 being configured to adjust the pulse width 60 accordingly.

In particular, the pulse width 60 or the amount of aerosol to be produced can be specified by a prescription and/or input by a user on the ventilator 1 and/or nebulizer 3. By way of example, a value for an amount of aerosol to be produced is set on the ventilator 1 and is converted into an appropriate pulse width 60 by the nebulizer 3.

By way of example, different modes of operation for the nebulizer 3 can be specified by way of the ventilator 1. By way of example, such a mode of operation can be designed such that the nebulizer 3 is always operated with optimum efficiency in the case of maximum aerosol production. A further mode of operation may be characterized in that the aerosol emission is matched to the patient's respiration, for example in such a way that aerosol is only produced during inspiration. It is also possible to provide a type of pulse width 60 ramp, by means of which the aerosol emission is increased and/or reduced over a period of time. In possible embodiments, the aerosol production is for example increased by a successive increase in the pulse width 60 of the RF signal 56 when inspiration starts and/or before inspiration starts and/or towards the end of expiration. Alternatively or in addition, a reduction in the pulse width 60 toward the end of inspiration may also be provided.

In some embodiments, the pulse width 60 is for example also adapted to the respiratory flow rates measured by the ventilator 1. By way of example, if the respiratory flow rate increases, the pulse width 60 or the rate of aerosol production is also increased.

Moreover, some embodiments also consider the aerosol production being activated in accordance with given times. By way of example, a varying amount of aerosol can be produced and supplied to the patient at different times. The times at which aerosol production is provided, and also the amount of aerosol to be produced, can for example be programmed by way of the ventilator 1. Provision can also be made for an automatic adjustment of the production of aerosol, in particular the rate or amount of produced aerosol, and the corresponding change in the pulse width 60, on the basis of physiological and/or medical data.

LIST OF REFERENCE SIGNS

1 Ventilator
2 Tube
3 Nebulizer
4 Tee joint
5 Membrane
6 Piezo element
7 Substrate plate
8 Liquid reservoir
9 Liquid
10 Housing
11 Lid
12 Electrical connection
13 Control electronics
14 Perforation
15 Aerosol droplet
16 Aerosol generator
17 Controller
18 A/D converter
19 Transformer
20 RF generator
21 Transistor (field effect; MOSFET)
22 Voltmeter
23 Ammeter
24 Ammeter
25 Electronics part
26 Nebulizer part
27 Housing part
28 Housing part
29 O-ring
30 Printed circuit board
31 Screw
32 Opening
33 Cable connector
34 Cable
35 Contact element
36 Insertion opening
37 Contact pins
38 Connecting piece (flange)
39 Frame (aerosol generator)
40 Connector receptacle (for flange)
41 Electronics contact
42 Leadthrough
43 Inductor
44 Resonant circuit
45 Mask connector
46 Filling device
47 Fill level indicator
48 Guide rail
49 Guide element
50 Guide groove
51 Latching position
52 Oscillator
53 Pulse width modulator
54 Boundary
55 Excitation signal
56 RF signal
57 Opening
58 Arcuate section
59 Wall
60 Pulse width To sum up, the present invention provides:

1. A nebulizer for producing an inhalable mist of droplets (aerosol), wherein the nebulizer comprises at least an aerosol generator, a housing having a liquid reservoir and control electronics, the aerosol generator consisting at least of a membrane, a piezo element and a substrate plate, and the control electronics comprising at least an RF generator, a controller, memory and switching elements, and an inductor, and wherein the aerosol generator forms a resonant circuit together with the inductor and the control electronics are configured so that they at least partly excite the aerosol generator to vibrate, the aerosol generator being configured such that aerosol droplets are producible by the vibrations and the RF generator being configured to vary the amount of aerosol produced.
2. The nebulizer of item 1, wherein the RF generator produces rectangular signals with a pulse width as RF signal.
3. The nebulizer of at least one of the preceding items, wherein the memory and switching elements of the control electronics are configured to produce an excitation signal from a rectangular signal and the resonant circuit.
4. The nebulizer of at least one of the preceding items, wherein the memory and switching elements comprise at least a transformer and a transistor, the transistor being configured, in conjunction with the transformer, to produce an excitation signal from a rectangular signal and the resonant circuit.
5. The nebulizer of at least one of the preceding items, wherein the control electronics are configured to specify an excitation frequency for the aerosol generator and/or the resonant circuit.

6. The nebulizer of item 2 or item 3, wherein the control electronics are configured to produce a sinusoidal excitation signal, a produced excitation signal having a higher voltage than the rectangular signal.
7. The nebulizer of least one of items 2 to 6, wherein the nebulizer is configured to control the amount of aerosol produced by way of the pulse width.
8. The nebulizer of item 7, wherein the pulse width of a rectangular signal reaches a maximum of about 50% or a maximum of about 30%.
9. The nebulizer of at least one of the preceding items, wherein the RF generator comprises at least an oscillator and a pulse width modulator, the pulse width modulator being configured to specify the pulse width of the rectangular signal.
10. The nebulizer of at least one of the preceding items, wherein the control electronics comprise at least a device for measuring a voltage, the device for measuring the voltage being arranged such that a voltage is recorded at the aerosol generator and the control electronics being configured to determine an optimal frequency of an excitation signal from the voltage measurement.
11. The nebulizer of item 10, wherein the control electronics are configured to determine the optimal excitation frequency by way of a voltage drop at the aerosol generator when the optimal excitation frequency is overshot, the optimal excitation frequency corresponding to a resonant frequency of the aerosol generator and/or of the resonant circuit.
12. The nebulizer of at least one of the preceding items, wherein the control electronics are configured to automatically determine an optimal excitation frequency and/or resonant frequency of the aerosol generator and/or resonant circuit, and/or to regularly check and automatically adjust said optimal excitation frequency and/or resonant frequency.
13. The nebulizer of at least one of the preceding items, wherein the control electronics comprise at least a device for measuring the current intensity on a primary and/or secondary side of a transformer and the control electronics are configured to determine a power on the primary and/or secondary side of the transformer by way of a voltage and a measured current intensity, the control electronics moreover being configured to determine the efficiency by way of a comparison of a determined power on the primary side of the transformer with a determined power on the secondary side of the transformer and to determine a maximum efficiency on the basis of a comparison of the powers of the transformer on the primary and secondary sides, and to link the maximum efficiency to the pulse width.
14. The nebulizer of at least one of the preceding items, wherein the nebulizer is connectable to a ventilator and the control electronics are configured to receive and implement specifications regarding the aerosol production from the ventilator.
15. The nebulizer of at least one of the preceding items, wherein the nebulizer comprises a nebulizer part and an electronics part, the electronics part comprising at least the control electronics and the nebulizer part comprising at least the aerosol generator and the liquid reservoir, the liquid reservoir being formed in such a way that a liquid is led to the membrane of the aerosol generator.
16. The nebulizer of item 15, wherein the aerosol generator is mounted in a frame in the nebulizer part, the frame comprising at least one opening through which the liquid is led to the membrane, and wherein the liquid reservoir is separated from an insertion opening for the electronics part by a wall, the wall terminating with an edge of the opening.
17. A method for adjusting the aerosol production of a nebulizer, wherein the method comprises at least one of:

finding a resonant frequency of the aerosol generator and/or of the resonant circuit, determining an optimal efficiency, adjusting a pulse width, adjusting an amount of aerosol produced/to be produced.

18. The method of item 17, wherein, for the purposes of finding the resonant frequency of the aerosol generator and/or of the resonant circuit, a range of excitation frequencies is sampled and, at the same time, a voltage at the aerosol generator is measured, the resonant frequency being reached when an increase in the excitation frequency leads to a drop in the measured voltage.
19. The method of item 17 or item 18, wherein a determination of the optimal efficiency comprises a measurement of a current intensity at a primary side and at a secondary side of a transformer, and a respective power for the primary side and for the secondary side is determined from a respective current intensity by way of a voltage, and an efficiency is determined from a comparison of the determined powers, and wherein a determination of the optimal efficiency further comprises a variation in the pulse width, a variation in the efficiency following a variation of the pulse width and the greatest determined efficiency being considered to be the optimal efficiency.
20. The method of at least one of items 17 to 19, wherein an adjustment of the amount of aerosol produced/to be produced comprises a variation of the pulse width, a reduction in the pulse width below a pulse width for an optimal efficiency resulting in a reduction of the amount of aerosol produced.
21. A ventilation system, wherein the ventilation system comprises at least a ventilator and a nebulizer as set forth in at least one of items 1 to 16, and wherein the ventilation system at least comprises control electronics for controlling the nebulizer.
22. The ventilation system of item 21, wherein the control electronics are at least partly arranged in the nebulizer and the ventilator comprises at least a control unit that is configured to transmit specifications relating to an aerosol production to the control electronics, the specifications comprising at least a setting regarding an amount, duration and/or time of the aerosol production.

What is claimed is:

1. A nebulizer for producing an inhalable mist of droplets (aerosol), wherein the nebulizer comprises at least an aerosol generator, a housing having a liquid reservoir and control electronics, the aerosol generator comprising at least a membrane, a piezo element and a substrate plate, and the control electronics comprising at least a radiofrequency (RF) generator, a controller, memory and switching elements, and an inductor, and wherein the aerosol generator forms a resonant circuit together with the inductor, the control electronics are configured so that they at least partly excite the aerosol generator to vibrate, the aerosol generator being configured such that aerosol droplets are producible by the vibrations, and the RF generator being configured to vary an amount of aerosol produced, and wherein the control electronics further comprise at least a device for measuring a current intensity on a primary and/or a secondary side of at least a transformer and the control electronics are configured to determine a power on the primary and/or the secondary side of at least the transformer by way of a voltage and a measured current intensity, the control electronics moreover being configured to determine a efficiency by way of a comparison of a determined power on the primary side of the transformer with a determined power on the secondary side of at least the transformer and to determine a maximum efficiency on the basis of a comparison of the determined powers on the primary side and the secondary side of at least the transformer, and to link the maximum efficiency to a pulse width.

2. The nebulizer of claim 1, wherein the RF generator is configured to produce rectangular signals with the pulse width as a RF signal.

3. The nebulizer of claim 2, wherein the control electronics are configured to produce a sinusoidal excitation signal, and a produced excitation signal having a higher voltage than the rectangular signal.

4. The nebulizer of claim 2, wherein the RF generator of the nebulizer is configured to control the amount of aerosol produced by way of the pulse width.

5. The nebulizer of claim 4, wherein the pulse width of the rectangular signals reaches a maximum of about 50%.

6. The nebulizer of claim 2, wherein the RF generator comprises at least an oscillator and a pulse width modulator, the pulse width modulator being configured to specify the pulse width of the rectangular signals.

7. The nebulizer of claim 1, wherein the memory and switching elements of the control electronics are configured to produce an excitation signal from a rectangular signal and the resonant circuit.

8. The nebulizer of claim 1, wherein the memory and switching elements further comprise a transistor, the transistor being configured, in conjunction with the transformer, to produce an excitation signal from a rectangular signal and the resonant circuit.

9. The nebulizer of claim 1, wherein the control electronics are configured to specify an excitation frequency for the aerosol generator and/or the resonant circuit.

10. The nebulizer of claim 1, wherein the control electronics further comprise at least a device for measuring a voltage, the device for measuring the voltage being arranged such that the voltage is recorded at the aerosol generator and the control electronics being configured to determine an optimal frequency of an excitation signal from the voltage measurement.

11. The nebulizer of claim 10, wherein the control electronics are configured to determine the optimal excitation frequency by way of a voltage drop at the aerosol generator when an increase in the excitation frequency occurs, the optimal excitation frequency corresponding to a resonant frequency of the aerosol generator and/or of the resonant circuit.

12. The nebulizer of claim 1, wherein the control electronics are configured to automatically a) determine an optimal excitation frequency and/or a resonant frequency of the aerosol generator and/or the resonant circuit; and/or b) regularly check and automatically adjust said optimal excitation frequency and/or the resonant frequency.

13. The nebulizer of claim 1, wherein the nebulizer is connectable to a ventilator and the control electronics are configured to receive and implement specifications regarding an aerosol production from the ventilator.

14. The nebulizer of claim 1, wherein the housing of the nebulizer further comprises a nebulizer part and an electronics part, the electronics part comprising the control electronics and the nebulizer part comprising at least the aerosol generator and the liquid reservoir, the liquid reservoir being formed in such a way that a liquid is led to the membrane of the aerosol generator.

15. The nebulizer of claim 14, wherein the aerosol generator is mounted in a frame in the nebulizer part, the frame comprising at least one opening through which the liquid is led to the membrane, and wherein the liquid reservoir is separated from an insertion opening for the electronics part by a wall, the wall terminating with an edge of the opening.

16. A method for adjusting an aerosol production of a nebulizer of claim 1, wherein the method comprises at least one of:

a) finding a resonant frequency of the aerosol generator and/or of the resonant circuit, b) determining an optimal efficiency, c) adjusting the pulse width, and d) adjusting the amount of aerosol produced/to be produced.

17. The method of claim 16, wherein, for the purposes of finding the resonant frequency of the aerosol generator and/or of the resonant circuit, a range of excitation frequencies is sampled and, at the same time, a voltage at the aerosol generator is measured, the resonant frequency being reached when an increase in an excitation frequency leads to a drop in the measured voltage.

18. A ventilation system, wherein the ventilation system comprises at least a ventilator and a nebulizer of claim 1, and control electronics for controlling the nebulizer.

19. The ventilation system of claim 18, wherein the ventilator comprises at least a control unit that is configured to transmit specifications relating to an aerosol production to the control electronics of the nebulizer, the specifications comprising at least a setting regarding an amount, a duration and/or a time of the aerosol production.

* * * * *